United States Patent
Hunter et al.

(10) Patent No.: US 11,457,945 B2
(45) Date of Patent: Oct. 4, 2022

(54) ULTRASONIC BLADE AND CLAMP ARM ALIGNMENT FEATURES

(71) Applicant: ETHICON LLC, Guaynabo, PR (US)

(72) Inventors: Morgan R. Hunter, Cincinnati, OH (US); Brian D. Black, Loveland, OH (US); Thomas B. Remm, Milford, OH (US); Karl W. Mueller, Loveland, OH (US)

(73) Assignee: Cilag GmbH International, Zug (CH)

( * ) Notice: Subject to any disclaimer, the term of this patent is extended or adjusted under 35 U.S.C. 154(b) by 246 days.

(21) Appl. No.: 16/556,635

(22) Filed: Aug. 30, 2019

(65) Prior Publication Data

US 2021/0059708 A1 Mar. 4, 2021

(51) Int. Cl.
*A61B 17/32* (2006.01)
*A61B 17/285* (2006.01)
(Continued)

(52) U.S. Cl.
CPC .... *A61B 17/320092* (2013.01); *A61B 17/285* (2013.01); *A61B 17/29* (2013.01); *A61B 17/320068* (2013.01); *A61B 17/2816* (2013.01); *A61B 2017/00477* (2013.01); *A61B 2017/320071* (2017.08); *A61B 2017/320074* (2017.08);
(Continued)

(58) Field of Classification Search
CPC ... A61B 17/2816; A61B 17/285; A61B 17/29; A61B 17/320068; A61B 17/320092; A61B 2017/00477; A61B 2017/320071; A61B 2017/320074; A61B 2017/320093; A61B 2017/320094
See application file for complete search history.

(56) References Cited

U.S. PATENT DOCUMENTS

| 5,322,055 A | 6/1994 | Davison et al. |
| 5,873,873 A | 2/1999 | Smith et al. |

(Continued)

FOREIGN PATENT DOCUMENTS

WO    WO 2019/018289 A1    1/2019

OTHER PUBLICATIONS

U.S. Appl. No. 16/556,625, entitled "Ultrasonic Surgical Instrument with Axisymmetric Clamping," filed Aug. 30, 2019.

(Continued)

*Primary Examiner* — Ashley L Fishback
(74) *Attorney, Agent, or Firm* — Frost Brown Todd LLC

(57) ABSTRACT

A surgical instrument includes an end effector, a shaft assembly, and an axial location feature. The end effector includes an ultrasonic blade and a clamp arm that can move between an open and closed position. The shaft assembly includes a proximal shaft portion, an acoustic waveguide extending proximally from the ultrasonic blade, a distal shaft portion extending along a distal axis, and an articulation section interposed between the proximal shaft portion and the distal shaft portion. The articulation section can deflect the distal shaft portion and the end effector relative to the longitudinal axis between a non-deflected position and a deflected position. The axial location feature can inhibit the ultrasonic blade from shifting relative to the clamp arm along the distal axis as the end effector is driven between the non-deflected position and the deflected position.

12 Claims, 28 Drawing Sheets

(51) Int. Cl.
*A61B 17/29* (2006.01)
*A61B 17/28* (2006.01)
*A61B 17/00* (2006.01)

(52) U.S. Cl.
CPC ............ *A61B 2017/320093* (2017.08); *A61B 2017/320094* (2017.08); *A61B 2017/320095* (2017.08)

(56) References Cited

U.S. PATENT DOCUMENTS

| | | |
|---|---|---|
| 5,980,510 A | 11/1999 | Tsonton et al. |
| 6,325,811 B1 | 12/2001 | Messerly |
| 6,500,176 B1 | 12/2002 | Truckai et al. |
| 6,773,444 B2 | 8/2004 | Messerly |
| 6,783,524 B2 | 8/2004 | Anderson et al. |
| 6,887,252 B1 | 5/2005 | Okada et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,911,460 B2 | 12/2014 | Neurohr et al. |
| 9,023,071 B2 | 5/2015 | Miller et al. |
| 9,095,367 B2 | 8/2015 | Olson et al. |
| 9,301,759 B2 | 4/2016 | Spivey et al. |
| 9,314,308 B2 | 4/2016 | Parihar et al. |
| 9,381,058 B2 | 7/2016 | Houser et al. |
| 9,393,037 B2 | 7/2016 | Olson et al. |
| 9,402,682 B2 | 8/2016 | Worrell et al. |
| 9,949,785 B2 | 4/2018 | Price et al. |
| 10,034,683 B2 | 7/2018 | Monroe et al. |
| 10,172,636 B2 | 1/2019 | Stulen et al. |
| 10,226,274 B2 | 3/2019 | Worrell et al. |
| 10,258,363 B2 | 4/2019 | Worrell et al. |
| 10,327,797 B2 | 6/2019 | Conlon et al. |
| 10,342,567 B2 | 7/2019 | Hibner et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2011/0087212 A1 | 4/2011 | Aldridge et al. |
| 2012/0116265 A1 | 5/2012 | Houser et al. |
| 2015/0080924 A1* | 3/2015 | Stulen ............ A61B 17/320068 606/169 |
| 2015/0320438 A1 | 11/2015 | Weisenburgh, II et al. |
| 2016/0302818 A1 | 10/2016 | Weisenburgh, II et al. |
| 2016/0302819 A1 | 10/2016 | Stulen et al. |
| 2017/0281217 A1 | 10/2017 | Hibner |
| 2017/0281218 A1 | 10/2017 | Timm |
| 2017/0281219 A1 | 10/2017 | Hibner et al. |
| 2017/0281220 A1 | 10/2017 | Hibner et al. |
| 2017/0281221 A1 | 10/2017 | Boudreaux |

OTHER PUBLICATIONS

U.S. Appl. No. 16/556,661, entitled "Ultrasonic Surgical Instrument with a Multi-Planar Articulating Shaft Assembly," filed Aug. 30, 2019.
U.S. Appl. No. 16/556,667, entitled "Ultrasonic Transducer Alignment of an Articulating Ultrasonic Surgical Instrument," filed Aug. 30, 2019.
U.S. Appl. No. 16/556,727, entitled "Rotatable Linear Actuation Mechanism," filed Aug. 30, 2019.
U.S. Appl. No. 61/410,603, entitled "Energy-Based Surgical Instruments," filed Nov. 5, 2010.
International Search Report and Written Opinion dated Nov. 2, 2020 for Application No. PCT/IB2020/057742, 11 pgs.

\* cited by examiner

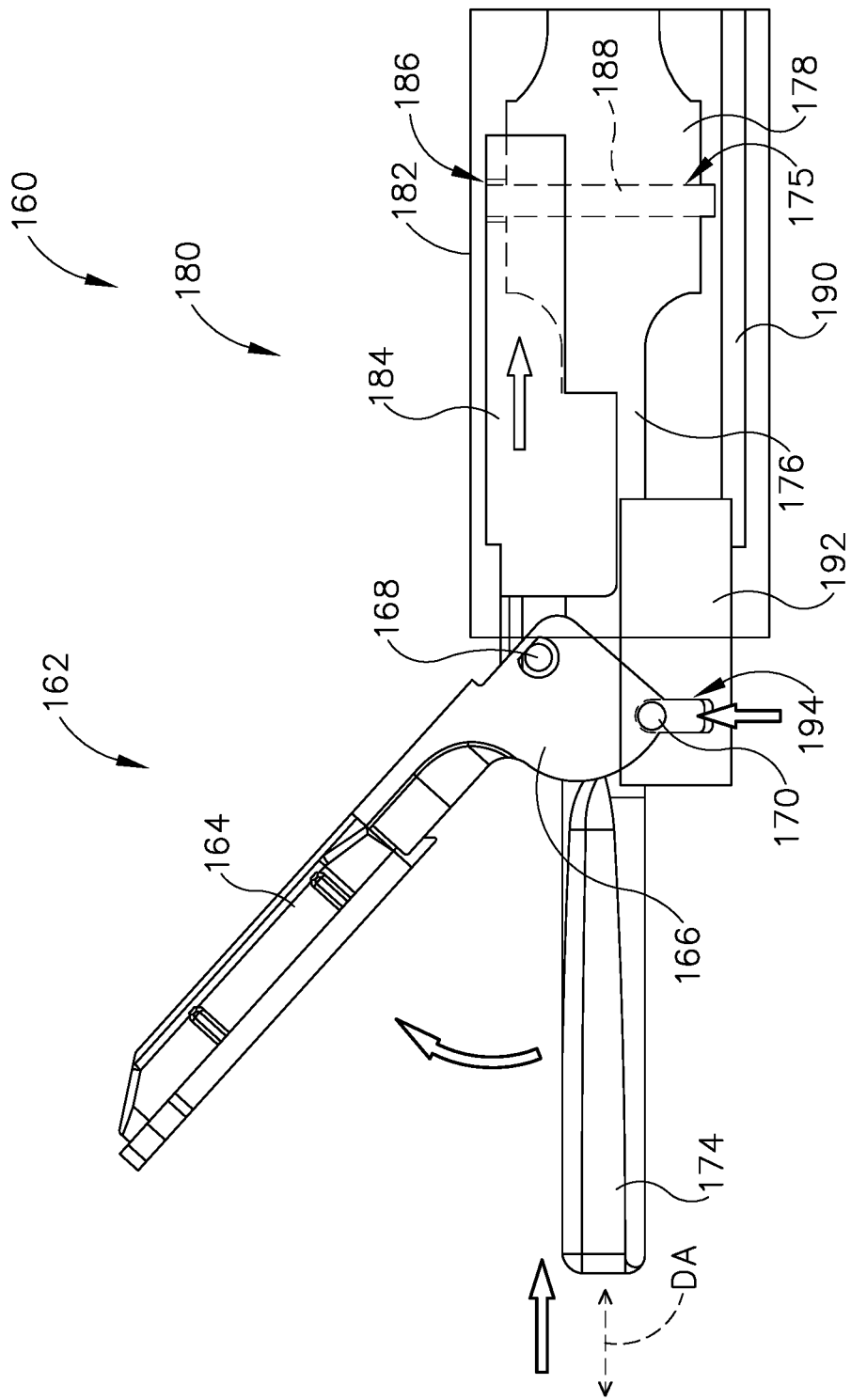

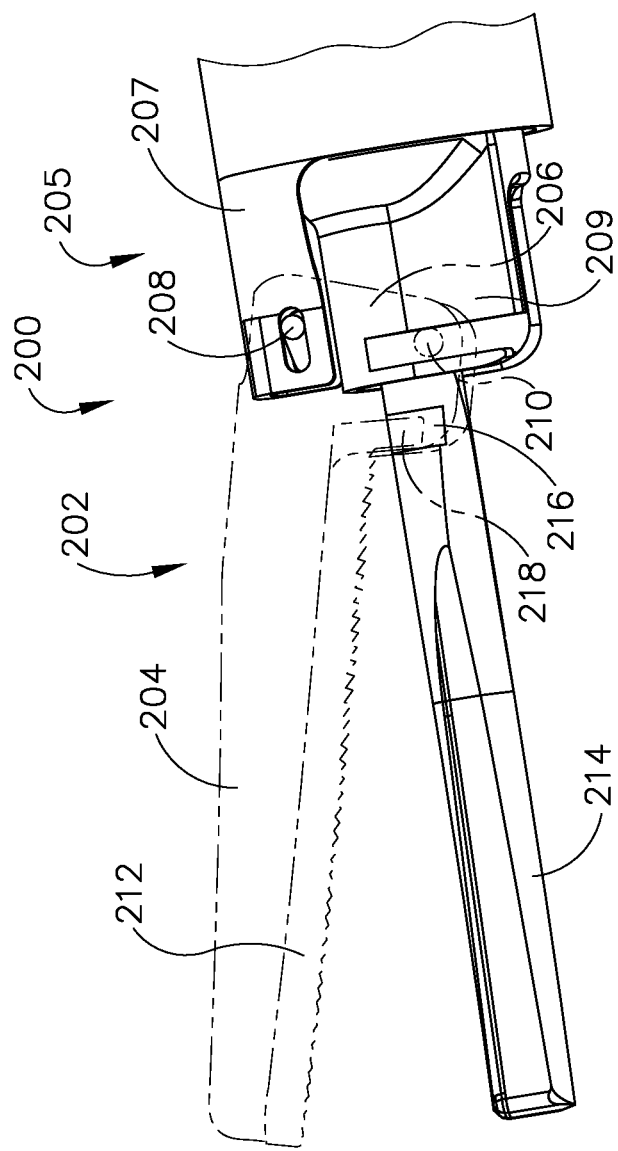
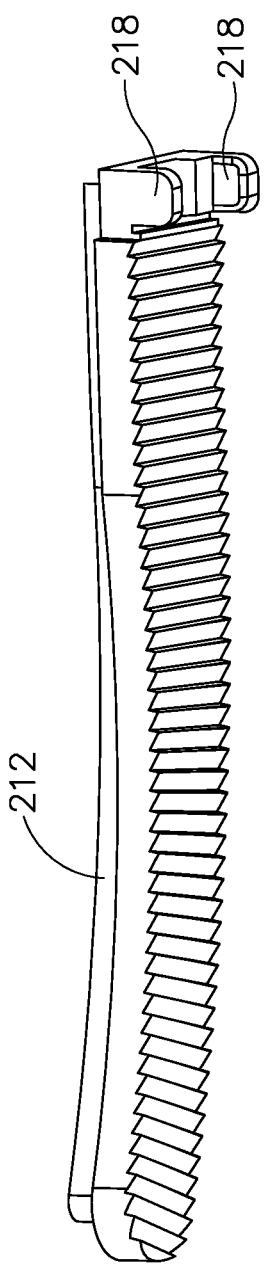
Fig.13
Fig.14

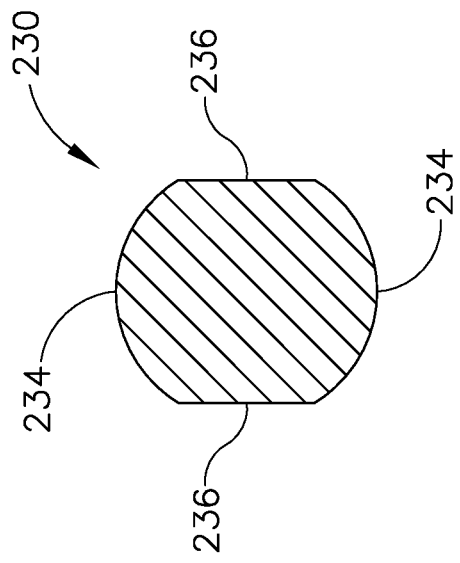
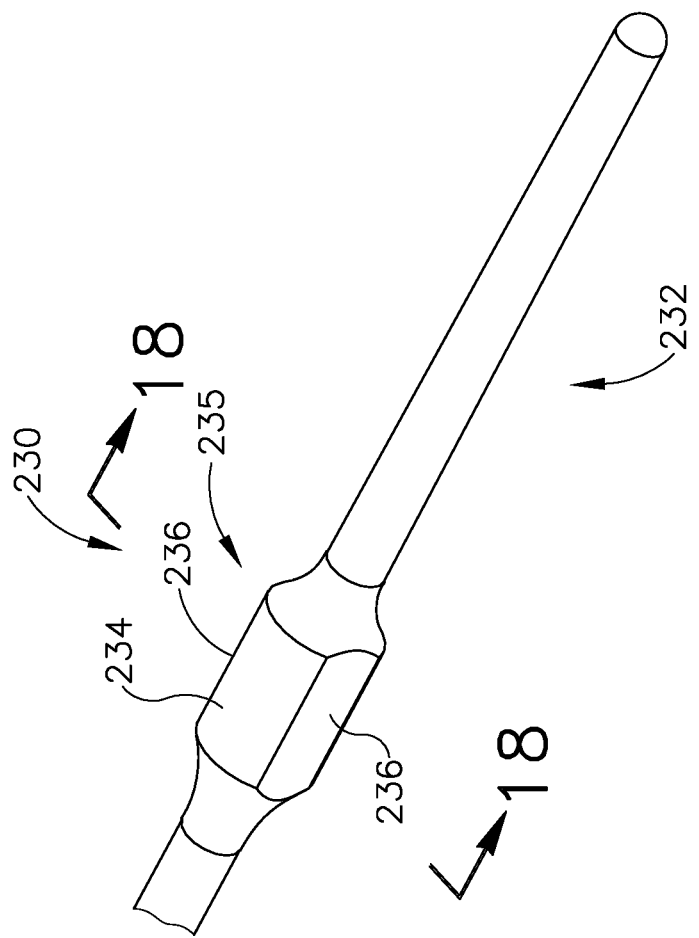

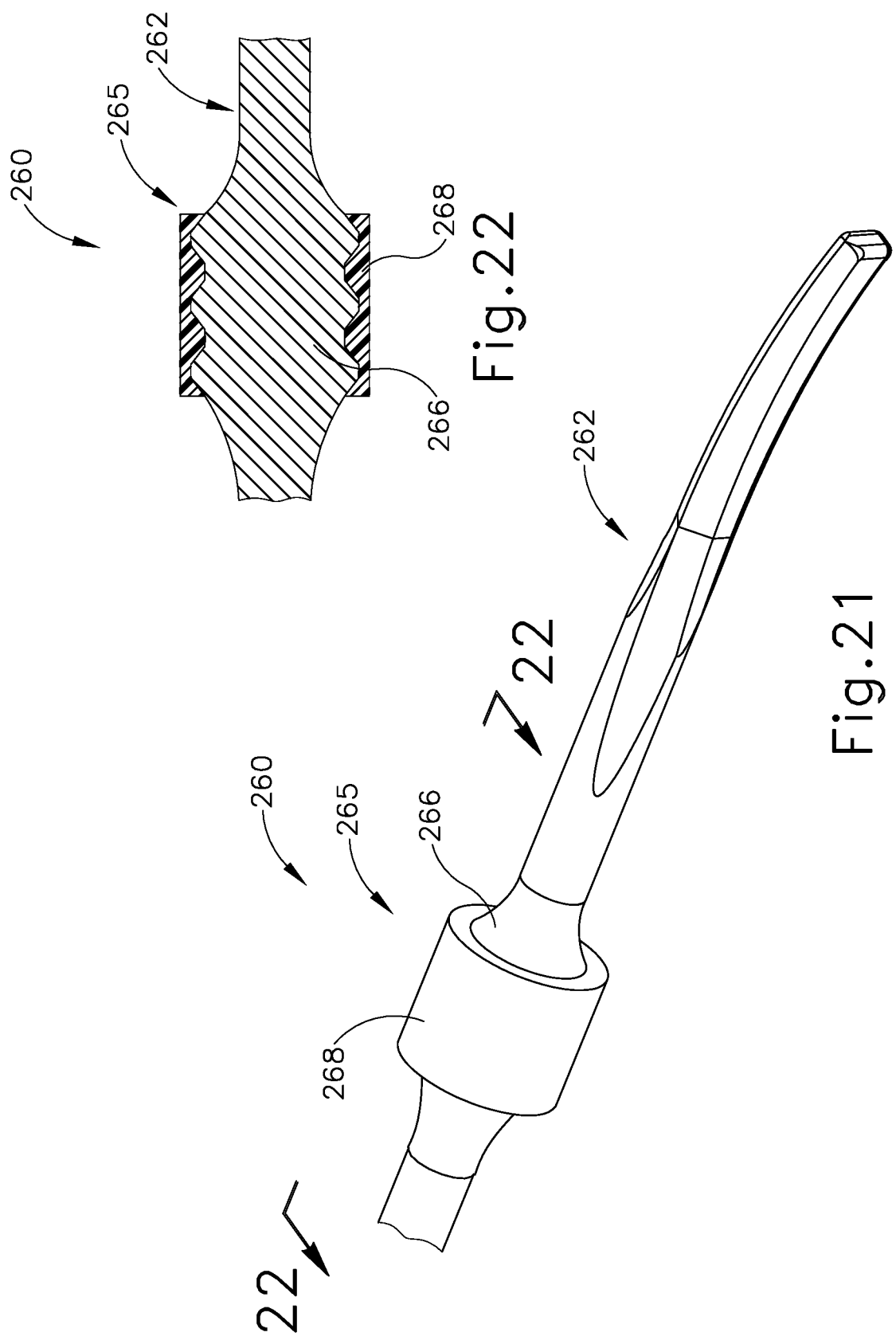

ULTRASONIC BLADE AND CLAMP ARM ALIGNMENT FEATURES

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Such surgical instruments may be directly gripped and manipulated by a surgeon or incorporated into a robotically assisted surgery. During robotically assisted surgery, the surgeon typically operates a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller typically includes one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; U.S. Pat. No. 9,095,367, issued Aug. 4, 2015, entitled "Flexible Harmonic Waveguides/Blades for Surgical Instruments," the disclosure of which is incorporated by reference herein; U.S. Pat. No. 10,226,274, issued Mar. 12, 2019, entitled "Ultrasonic Surgical Instrument with Articulation Joint Having Plurality of Locking Positions," the disclosure of which is incorporated by reference herein; U.S. Pat. No. 10,034,683, entitled "Ultrasonic Surgical Instrument with Rigidizing Articulation Drive Members," issued Jul. 31, 2018, the disclosure of which is incorporated by reference herein; U.S. Pat. Pub. No. 2016/0302818, published Oct. 10, 2016, entitled "Ultrasonic Surgical Instrument with Movable Rigidizing Member," the disclosure of which is incorporated by reference herein; U.S. Pat. Pub. No. 2016/0302819, published Oct. 20, 2016, entitled "Ultrasonic Surgical Instrument with Articulating End Effector having a Curved Blade," the disclosure of which is incorporated by reference herein; U.S. Pat. No. 10,342,567, issued Jul. 9, 2019, entitled "Ultrasonic Surgical Instrument with Opposing Thread Drive for End Effector Articulation," the disclosure of which is incorporated by reference herein; U.S. Pat. Pub. No. 2015/0320438, published Nov. 12, 2015, entitled "Ultrasonic Surgical Instrument with End Effector Having Restricted Articulation," the disclosure of which is incorporated by reference herein; U.S. Pat. Pub. No. 2017/0281217, published Oct. 5, 2017, entitled "Surgical Instrument with Dual Mode Articulation Drive," the disclosure of which is incorporated by reference herein; U.S. Pat. Pub. No. 2017/0281218, published Oct. 5, 2017, entitled "Surgical Instrument with Motorized Articulation Drive in Shaft Rotation Knob," the disclosure of which is incorporated by reference herein; U.S. Pat. Pub. No. 2017/0281219, published Oct. 5, 2017, entitled "Surgical Instrument with Locking Articulation Drive Wheel," the disclosure of which is incorporated by reference herein; U.S. Pat. Pub. No. 2017/0281220, published Oct. 5, 2017, entitled "Surgical Instrument with Selectively Locked Articulation Assembly," the disclosure of which is incorporated by reference herein; and U.S. Pat. Pub. No. 2017/0281221, published Oct. 5, 2017, entitled "Articulation Joint for Surgical Instrument," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11B depicts an elevational side view of the ultrasonic surgical instrument similar to FIG. 11A, but with the end effector in the open position and the shaft assembly in a first articulated configuration;

FIG. 13 depicts a perspective view of a fifth surgical instrument;

FIG. 14 depicts a perspective view of a clamp pad of the ultrasonic surgical instrument of FIG. 13;

FIG. 17 depicts a perspective view of a first example of a flanged acoustic waveguide and an ultrasonic blade that may be readily incorporated into the ultrasonic surgical instrument of FIG. 1;

FIG. 18 depicts a cross-sectional view of the acoustic waveguide of FIG. 17, taken along sectional line 18-18 of FIG. 17;

FIG. 21 depicts a perspective view of a fourth example of a flanged acoustic waveguide and an ultrasonic blade that may be readily incorporated into the ultrasonic surgical instrument of FIG. 1;

FIG. 22 depicts a cross-sectional view of the acoustic waveguide of FIG. 21, taken along sectional line 22-22 of FIG. 21;

Figure 1:
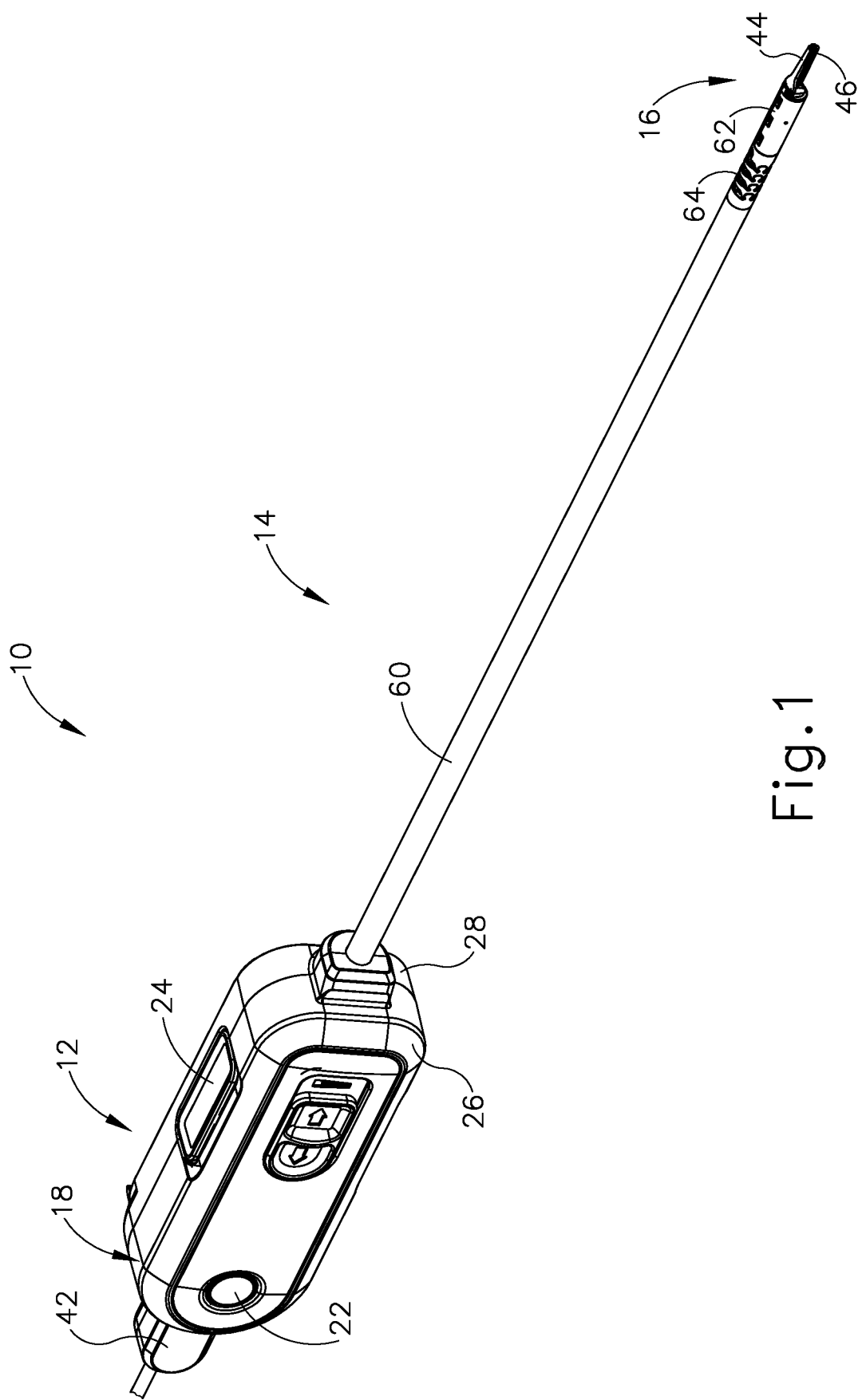
FIG. 1 depicts a front perspective view of a first ultrasonic surgical instrument having an end effector, a shaft assembly, and a base assembly configured to connect to a robotic driven interface.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary first surgical instrument, such as an ultrasonic surgical instrument (10). At least part of ultrasonic surgical instrument (10) may be constructed and operable in accordance with at least some of the teachings of any of the various patents, patent application publications, and patent applications that are cited herein. As described therein and as will be described in greater detail below, ultrasonic surgical instrument (10) is operable to cut tissue and seal or weld tissue (e.g., a blood vessel, etc.) substantially simultaneously. While the present example incorporates various ultrasonic features as ultrasonic surgical instrument (10), the invention is not intended to be unnecessarily limited to the ultrasonic features described herein.

Ultrasonic surgical instrument (10) of the present example comprises a body assembly, such as a base assembly (12), a shaft assembly (14), and an end effector (16). Base assembly (12) includes a housing (18), a button (22), and a pair of latch clasps (24). Button (22) is operatively connected to an electrical base power controller (not shown) and configured to selectively power ultrasonic surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (30) (see FIG. 5) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

Figure 2:
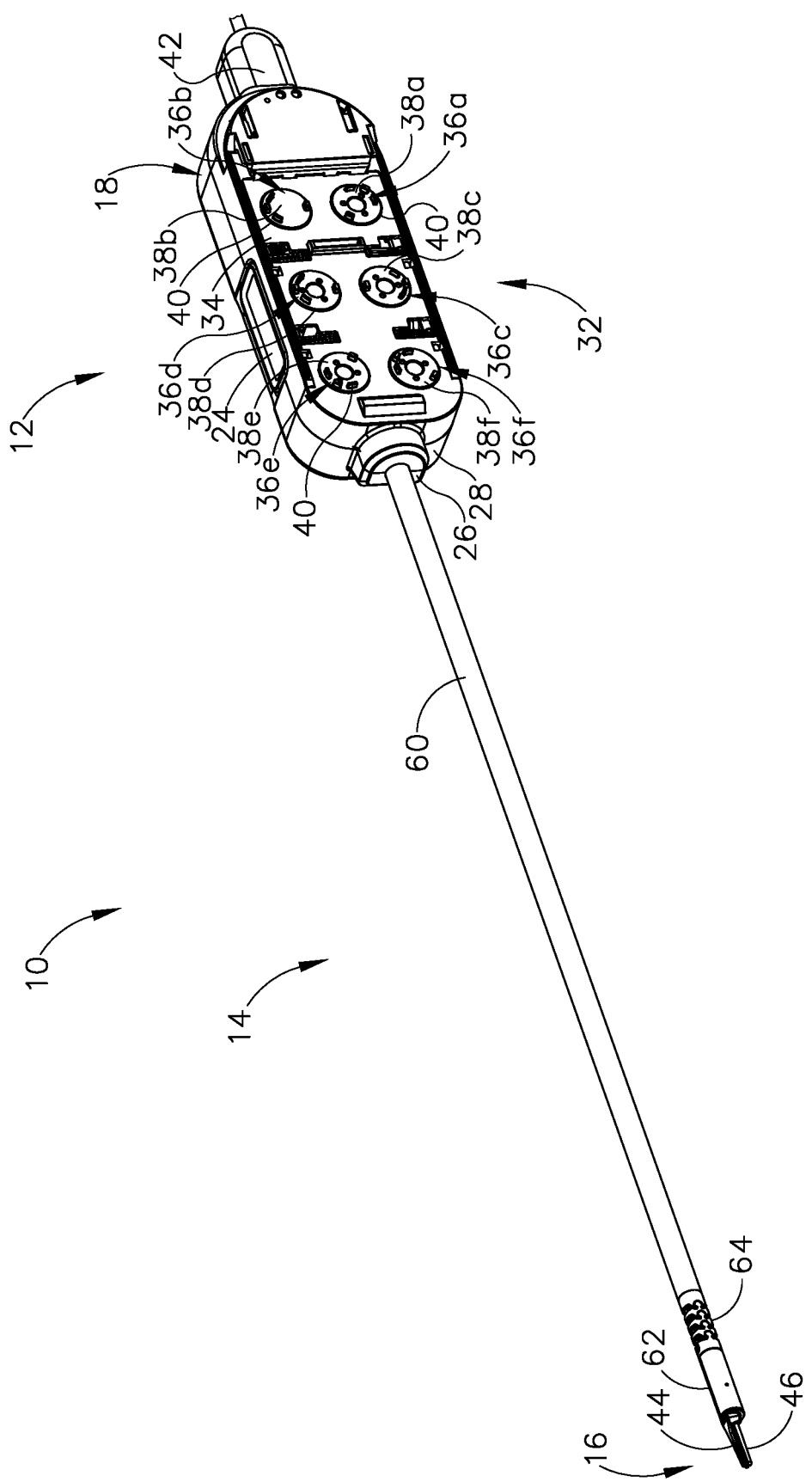
FIG. 2 depicts a rear perspective view of the ultrasonic surgical instrument of FIG. 1.

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (36a, 36b, 36c, 36d, 36e, 36f) having a plurality of input bodies (38a, 38b, 38c, 38d, 38e, 38f), respectively. Each input body (38a, 38b, 38c, 38d, 38e, 38f), which may also be referred to herein as a "puck," is configured to removably connect with the robotic drive (not shown) and, in the present example, is generally cylindrical and rotatable about an axis. Input bodies (38a, 38b, 38c, 38d, 38e, 38f) have a plurality of slots (40) configured to receive portions of the robotic drive (not shown) for gripping and rotatably driving input bodies (38a, 38b, 38c, 38d, 38e, 38f) in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16) associated with cutting, sealing, or welding tissue.

A. Exemplary End Effector and Acoustic Drivetrain

Figure 3A:
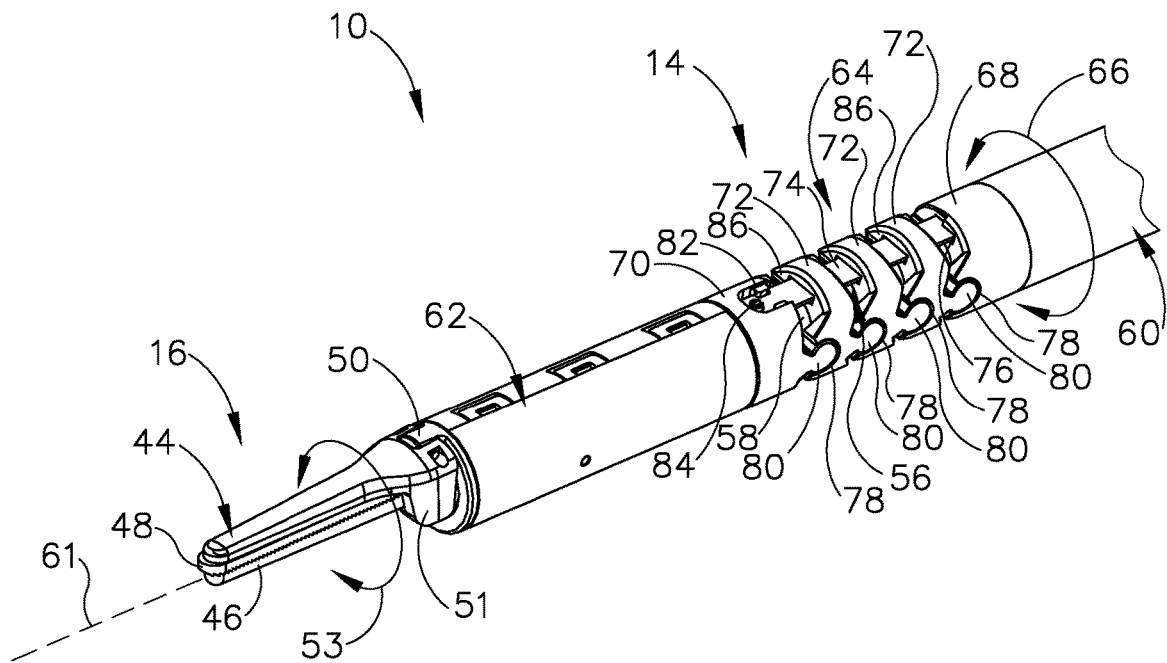
FIG. 3A depicts an enlarged perspective view of the ultrasonic surgical instrument of FIG. 1 with the end effector in a closed position and the shaft assembly in a straight configuration.
Figure 3B:
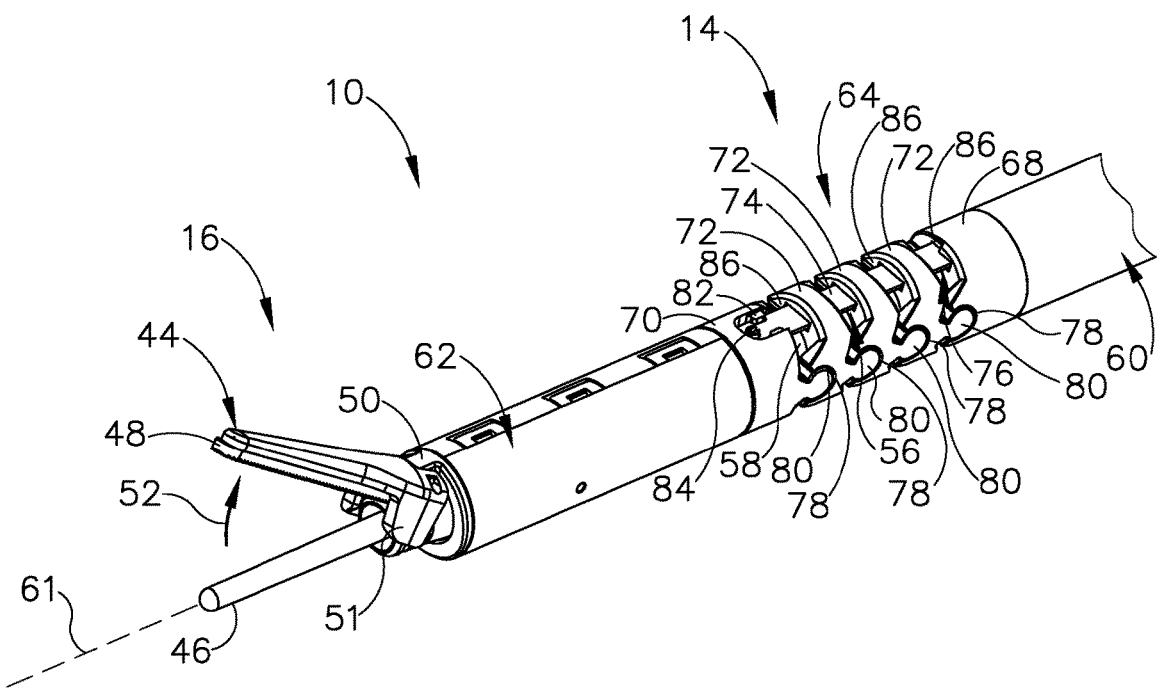
FIG. 3B depicts the enlarged perspective view of the ultrasonic surgical instrument similar to FIG. 3A, but showing the end effector in an open position.

As best seen in FIGS. 3A-3B, end effector (16) of the present example includes a clamp arm (44) and an ultrasonic blade (46). Clamp arm (44) has a clamp pad (48) secured to an underside of clamp arm (44), facing blade (46). In one example, clamp pad (48) may comprise polytetrafluoroethylene (PTFE) and/or any other suitable material(s). Clamp arm (44) is pivotally secured to a distally projecting tongue (50) of shaft assembly (14). Clamp arm (44) is operable to selectively pivot toward and away from blade (46) to selectively clamp tissue between clamp arm (44) and blade (46). A pair of arms (51) extend transversely from clamp arm (44) and are pivotally secured to another portion of shaft assembly (14) configured to longitudinally slide to pivot clamp arm (44) as indicated by an arrow (52) between a closed position shown in FIG. 3A and an open position shown in FIG. 3B.

In addition to pivoting relative to blade (46), clamp arm (44) of the present example is further configured to rotate about blade (46) relative to blade (46) and also relative to shaft assembly (14) as indicated by an arrow (53). In one example, clamp arm (44) rotates in the clockwise or counterclockwise directions completely around blade (46) and may be selectively fixed in any angular position relative to blade (46) for directing clamp arm (44) from the open position to the closed position for clamping tissue. In another example, clamp arm (44) may have rotational stops (not shown) configured to limit rotational movement of clamp arm (44) relative to blade (46) in one or more predetermined positions.

Blade (46) of the present example is operable to vibrate at ultrasonic frequencies in order to effectively cut through and seal tissue, particularly when the tissue is being compressed between clamp pad (48) and blade (46). Blade (46) is positioned at a distal end of an acoustic drivetrain. This acoustic drivetrain includes a transducer assembly (54) (see FIG. 5) and an acoustic waveguide (56), which includes a flexible portion (58) discussed below in greater detail. It should be understood that waveguide (56) may be configured to amplify mechanical vibrations transmitted through waveguide (56). Furthermore, waveguide (56) may include features operable to control the gain of the longitudinal vibrations along waveguide (56) and/or features to tune waveguide (56) to the resonant frequency of the system. Various suitable ways in which waveguide (56) may be mechanically and acoustically coupled with transducer assembly (54) (see FIG. 5) will be apparent to those of ordinary skill in the art in view of the teachings herein.

Those of ordinary skill in the art will understand that, as a matter of physics, a distal end of blade (46) is located at a position corresponding to an anti-node associated with resonant ultrasonic vibrations communicated through flexible portion (58) of waveguide (56). When transducer assembly (54) (see FIG. 5) is energized, the distal end of blade (46) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (54) (see FIG. 5) of the present example is activated, these mechanical oscillations are transmitted through waveguide (56) to reach blade (46), thereby providing oscillation of blade (46) at the resonant ultrasonic frequency. Thus, when tissue is secured between blade (46) and clamp pad (48), the ultrasonic oscillation of blade (46) may simultaneously sever the tissue and denature the proteins in adjacent tissue cells, thereby providing a coagulative effect with relatively little thermal spread. In some versions, end effector (16) is operable to apply radiofrequency (RF) electrosurgical energy to tissue in addition to applying ultrasonic energy to tissue. In any case, other suitable configurations for an acoustic transmission assembly and transducer assembly (54) will be apparent to one of ordinary skill in the art in view of the teachings herein. Similarly, other suitable configurations for end effector (16) will be apparent to those of ordinary skill in the art in view of the teachings herein.

B. Exemplary Shaft Assembly and Articulation Section

As shown in FIGS. 3A-3B, shaft assembly (14) includes a proximal shaft portion (60) extending along a longitudinal axis (61), a distal shaft portion (62) distally projecting relative to the proximal shaft portion (60), and an articulation section (64) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (64) and/or end effector (16) about longitudinal axis (61). While end effector (16) generally rotates with shaft assembly (14) as indicated by arrow (66), end effector (16) may be simultaneously and independently rotated as indicated by arrow (53) relative to shaft assembly (14) during use for repositioning portions of shaft assembly (14) and/or end effector (16) as desired.

Articulation section (64) is configured to selectively position end effector (16) at various lateral deflection angles relative to longitudinal axis (61) defined by proximal shaft portion (60). Articulation section (64) may take a variety of forms. In the present example, articulation section (64) includes a proximal link (68), a distal link (70), and a plurality of intermediate links (72) connected in series between proximal and distal links (68, 70). Articulation section (64) further includes a pair of articulation bands (74) extending along a pair of respective channels (76) collectively defined through links (68, 70, 72). Links (68, 70, 72) are generally configured to pivot relative to each other upon actuation of articulation bands (74) to thereby bend articulation section (64) with flexible portion (58) of waveguide (56) therein to achieve an articulated state. By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095,367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034,683, entitled "Ultrasonic Surgical Instrument with Rigidizing Articulation Drive Members," issued on Jul. 31, 2018. Alternatively, articulation section (64) may be constructed and/or operable in any other suitable fashion.

Links (68, 70, 72) shown in FIGS. 3B-4B pivotally interlock to secure distal shaft portion (62) relative to proximal shaft portion (60) while allowing for deflection of distal shaft portion (62) relative to longitudinal axis (61). In the present example, proximal link (68) is rigidly connected to proximal shaft portion (60) and has a pair of arcuate grooves (78) opposed from each other. Intermediate links (72) respectively have a pair of arcuate tongues (80) proximally extending therefrom and a pair of arcuate grooves (78) positioned distally opposite from respective tongues (80). Each intermediate link (72) has tongues (80) pivotally received within adjacent arcuate grooves (78) of another intermediate link (72) or proximal link (68) as applicable. Distal link (70) is rigidly connected to distal shaft portion (62) and has another pair of arcuate tongues (80) opposed from each other and pivotally received within adjacent arcuate grooves (78) of intermediate link (72). Tongues (80) and grooves (78) connect together to form the series of interlocked links (68, 70, 72).

Figure 4A:
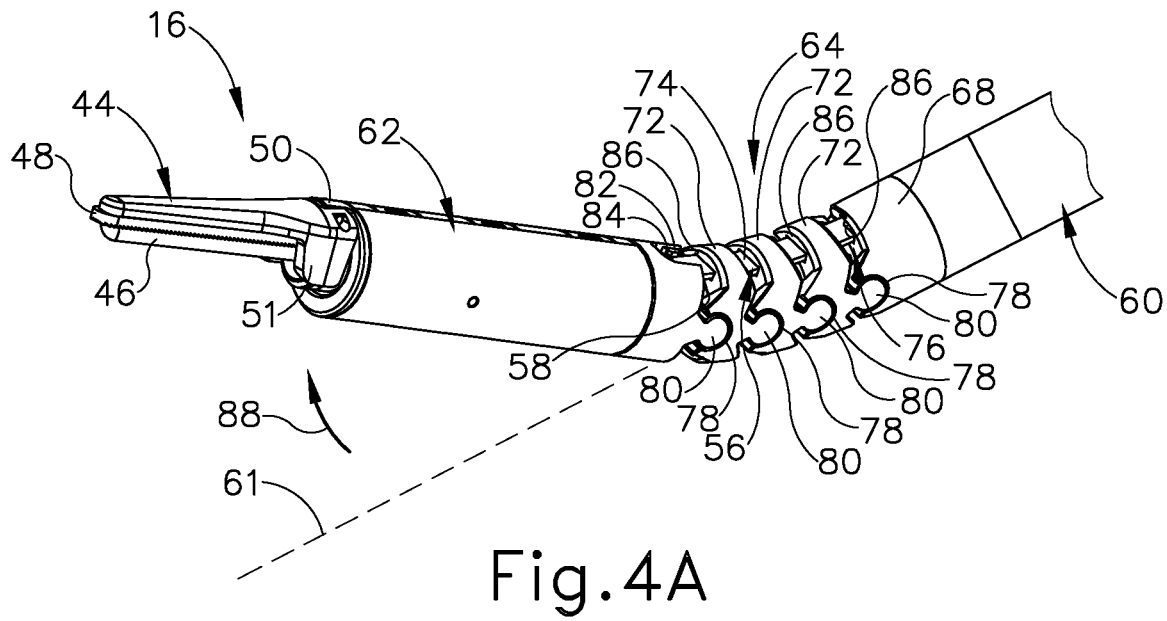
FIG. 4A depicts an enlarged perspective view of the ultrasonic surgical instrument of FIG. 1 with the end effector in a closed position and the shaft assembly in a first articulated configuration.
Figure 4B:
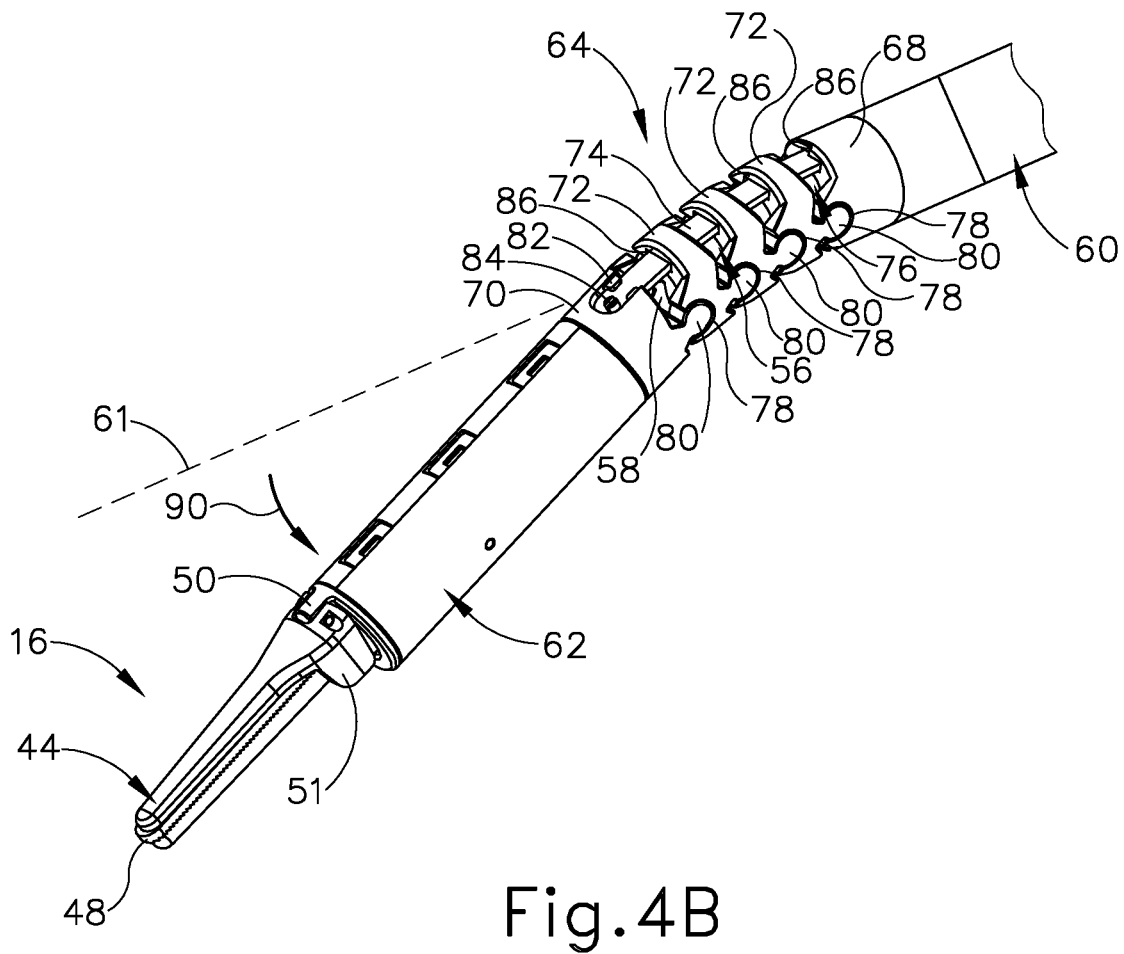
FIG. 4B depicts the enlarged perspective view of the ultrasonic surgical instrument similar to FIG. 4A, but with the shaft assembly in a second articulated configuration.

Distal link (70) further includes a pair of opposing notches (82) with a pin (84) therein configured to receive distal end portions of respective articulation bands (74). More particularly, pins (84) extend through a hole in each respective articulation bands (74) while distal end portions of respective articulation bands (74) are coupled within notches (82). Slots (86) in each of intermediate and proximal links (72, 68) longitudinally align with each other and notches (82) to collectively define channels (76) configured to receive articulation bands (74) while allowing articulation bands (74) to slide relative to links (68, 70, 72). To this end, when articulation bands (74) translate longitudinally in an opposing fashion, this will cause articulation section (64) to bend, thereby laterally deflecting end effector (16) away from the longitudinal axis (61) of proximal shaft portion (60) from a straight configuration as shown in FIG. 3B to a first articulated configuration as shown in FIG. 4A and indicated by an arrow (88) or a second articulated configuration as shown in FIG. 4B and indicated by an arrow (90). In particular, end effector (16) will be articulated toward the articulation band (74) that is being pulled proximally. During such articulation, the other articulation band (74) may be pulled distally. Alternatively, the other articulation band (74) may be driven distally by an articulation control. Furthermore, flexible acoustic waveguide (56) is configured to effectively communicate ultrasonic vibrations from waveguide (56) to blade (46) even when articulation section (64) is in an articulated configuration as shown in FIGS. 4A-4B.

C. Exemplary Base Assembly with Instrument Actuators for Robotic Interface

Figure 5:
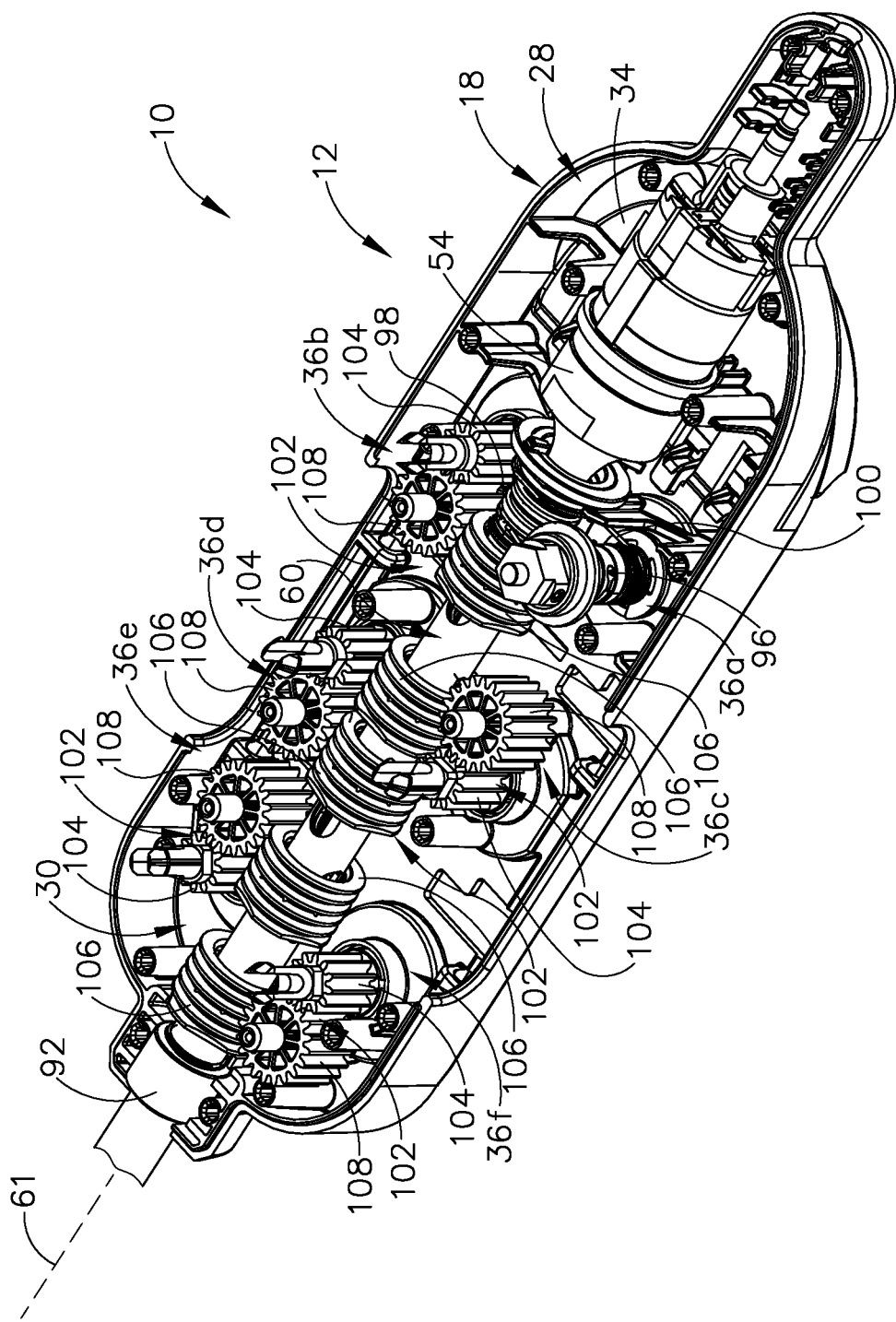
FIG. 5 depicts an enlarged perspective view of the ultrasonic surgical instrument of FIG. 1 with the base assembly having various components removed for greater clarity of an interior space of the base assembly.

FIG. 5 shows interior space (30) of base assembly (12) with instrument actuators (36a, 36b, 36c, 36d, 36e, 36f) in greater detail. Generally, instrument actuators (36a, 36b, 36c, 36d, 36e, 36f) are engaged with shaft assembly (14) and configured to direct movement of end effector (16) and/or shaft assembly (14), such as movement indicated above in one example by arrows (52, 53, 66, 88, 90) (see FIGS. 3A-4B). Shaft assembly (14) is received within base assembly (12) and supported by bearings (92) therein to operatively connect each respective instrument actuator (36a, 36b, 36c, 36d, 36e, 36f) to shaft assembly (14) as well as operatively connect acoustic waveguide (56) (see FIG. 3A) to transducer assembly (54) and a generator (not shown) of the acoustic drivetrain. More particularly, transducer assembly (54) is coupled with generator (not shown) such that transducer assembly (54) receives electrical power from generator (not shown). Piezoelectric elements (not shown) in transducer assembly (54) convert that electrical power into ultrasonic vibrations. Generator (not shown) may be coupled to the electrical power source (not shown) via electrical plug (42) (see FIG. 1) and a control module (not shown) that are configured to provide a power profile to transducer assembly (54) that is particularly suited for the generation of ultrasonic vibrations through transducer assembly (54). By way of example only, generator (not shown) may comprise a GEN04 or GEN11 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. Still other suitable forms that generator (not shown) may take, as well as various features and operabilities that generator (not shown) may provide, will be apparent to those of ordinary skill in the art in view of the teachings herein.

Figure 6:
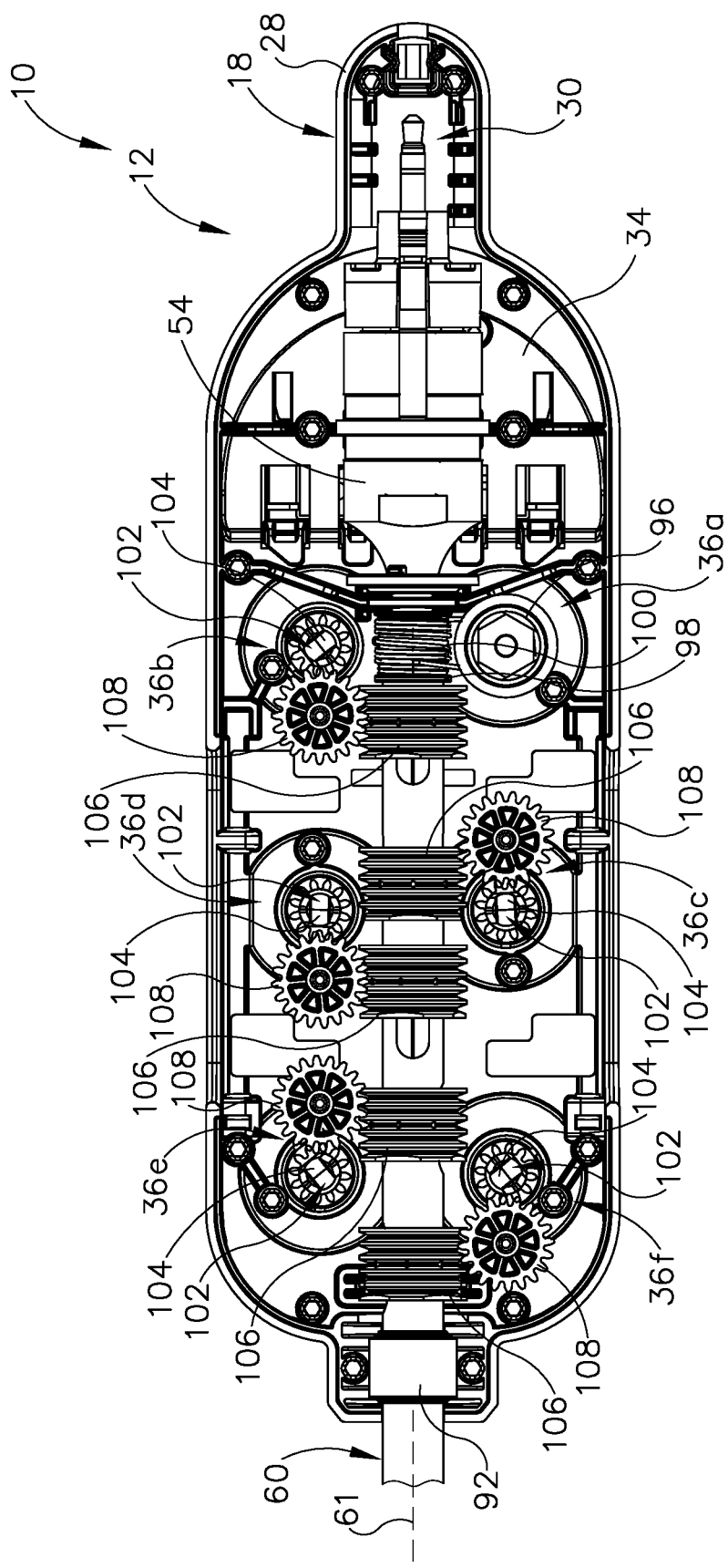
FIG. 6 depicts an enlarged front view of the ultrasonic surgical instrument of FIG. 1 with the base assembly having various components removed for greater clarity of the interior space of the base assembly.

The present example of base assembly (12) shown in FIGS. 5-6 includes six instrument actuators (36a, 36b, 36c, 36d, 36e, 36f), although it will be appreciated that any such number of such instrument actuators (36a, 36b, 36c, 36d, 36e, 36f) configured to direct movement of shaft assembly (14) and/or end effector (16) may be similarly used. As shown with respect to operation of ultrasonic surgical instrument (10), instrument actuator (36a) is more particularly a roll system actuator (36a) configured to rotate shaft assembly (14) about longitudinal axis (61). In contrast, instrument actuators (36b, 36c, 36d, 36e, 36f) are linear system actuators (36b, 36c, 36d, 36e, 36f) configured to translationally drive movement of portions of end effector (16) and/or shaft assembly (14) while simultaneously allowing for rotation of shaft assembly (14) via roll system actuator (36a).

Roll system actuator (36a) in one example includes a drive spool (96) rigidly connected to puck (38a) (see FIG. 2) and a driven spool (98) rigidly connected to proximal shaft portion (60) within housing (18). Drive spool (96) is mounted to rotate with puck (38a) (see FIG. 2) about a common puck axis, whereas driven spool (98) is mounted to rotate with proximal shaft portion (60) about the longitudinal axis (61). A cable (100) wraps around each of the drive and driven spools (96, 98), accommodating the differing orientation of the puck axis and longitudinal axis (61), such that rotating drive spool (96) via puck (38a) (see FIG. 2) urges rotation of driven spool (98). In turn, shaft assembly (14), including proximal and distal shaft portions (60, 62) rotates about longitudinal axis (61) as indicated by arrow (66) (see FIG. 3A), such as by robotically driven actuation of puck (38a) (see FIG. 2).

Linear system actuators (36b, 36c, 36d, 36e, 36f) of the present example include a gear-rack mechanism (102) having a rotatable drive gear (104), a translatable rack gear (106), and an idler gear (108) connected therebetween. Drive gears (104) are respectively connected to and rigidly project from pucks (38b, 38c, 38d, 38e, 38f) (see FIG. 2), whereas each rack gear (106) is connected to another portion of proximal shaft portion (60) directing movement of shaft assembly (14) and/or end effector (16) as discussed above. Each rack gear (106) is cylindrical and rigidly connected relative to proximal shaft portion (60) to rotate therewith. Rack gear (106) is thereby configured to rotate with shaft assembly (14) while remaining meshed with idler gear (108). Rotating respective pucks (38b, 38c, 38d, 38e, 38f) (see FIG. 2) thus respectively rotates drive gears (104) and idler gears (108) to translate rack gears (106) as desired.

In the present example, with respect to FIGS. 2-4B and FIG. 6, linear system actuator (36b) has puck (38b) operatively connected to clamp arm (44) to direct movement of clamp arm (44) between the open and closed positions according to arrow (52). Linear systems (36c, 36d) have respective pucks (38c, 38d) operatively connected to clamp arm (44) to direct movement of clamp arm (44) around blade (46) in both the clockwise and counterclockwise directions according to arrow (53). In addition, linear system actuators (36e, 36f) have respective pucks (38e, 38f) operatively connected to articulation bands (74) to direct movement of articulation section (64) according to arrows (88, 90) for deflecting end effector (16) relative to longitudinal axis (61). Of course, in other examples, instrument actuators (36a, 36b, 36c, 36d, 36e, 36f) may be alternatively configured with more or less actuators (36a, 36b, 36c, 36d, 36e, 36f) and/or more or less movement as desired. The invention is thus not intended to be unnecessarily limited to instrument actuators (36a, 36b, 36c, 36d, 36e, 36f) or particular movements of shaft assembly (14) and/or end effector (16) as described in the present example.

II. Exemplary Alignment Features for Ultrasonic Blade and Clamp Arm

Figure 7A:
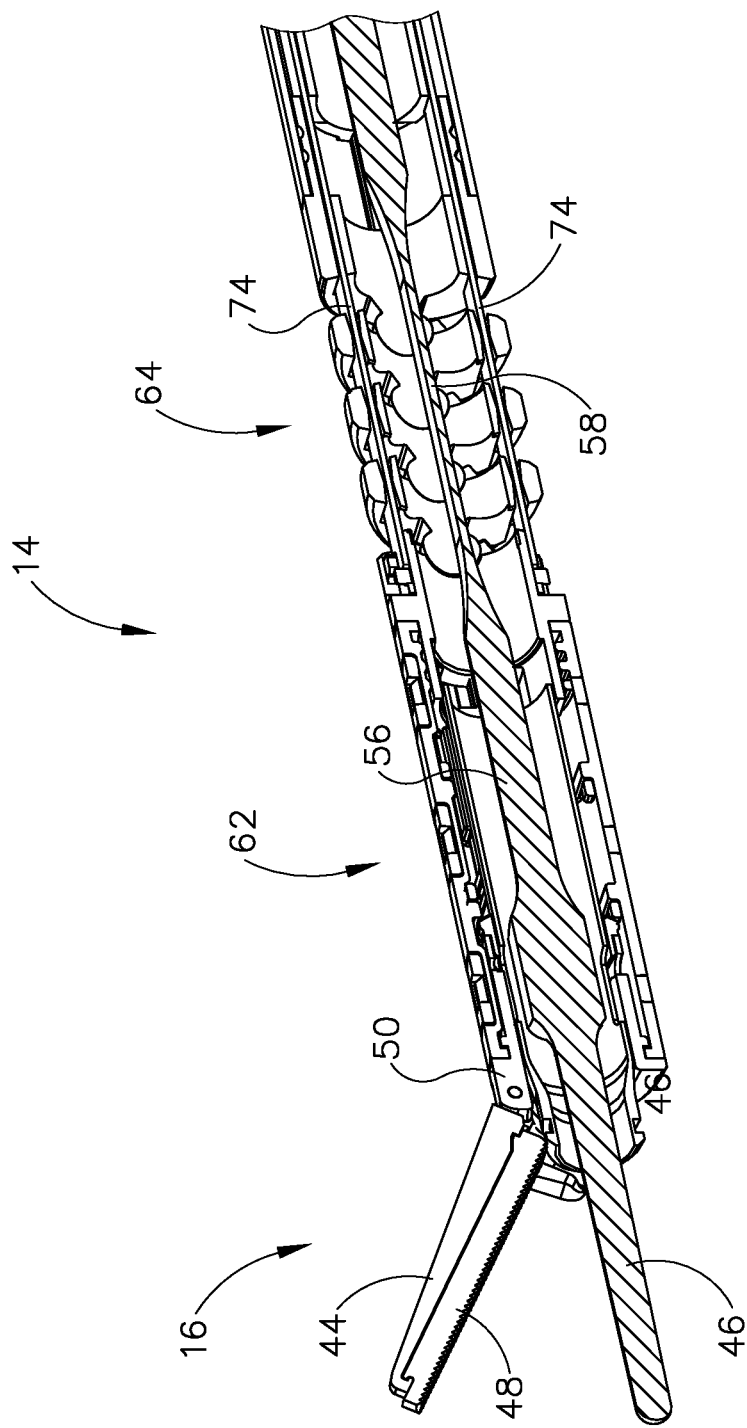
FIG. 7A depicts an enlarged sectional perspective view of the ultrasonic surgical instrument of FIG. 1 with the end effector in the open position and the shaft assembly in a non-articulated configuration.
Figure 7B:
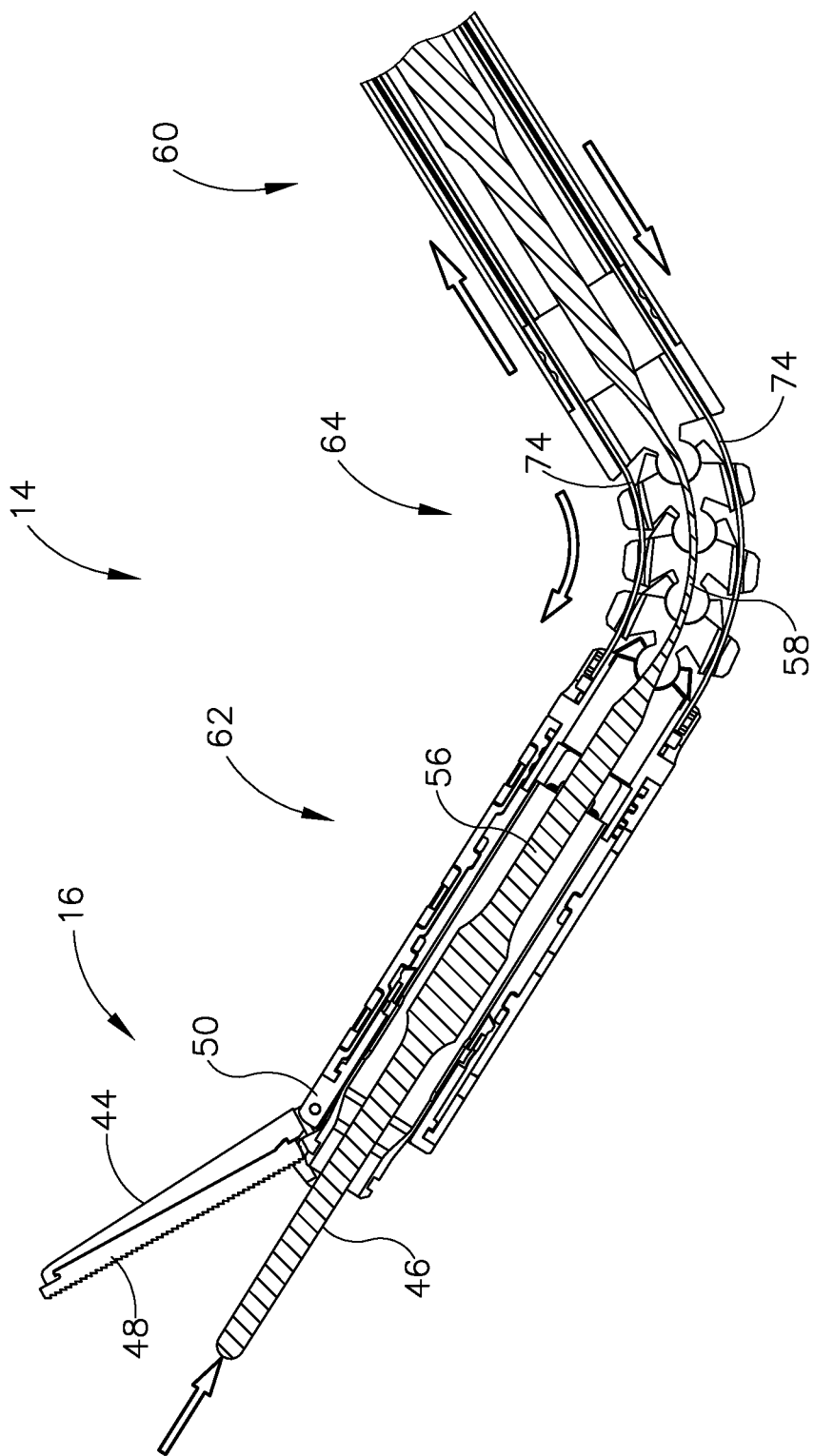
FIG. 7B depicts an enlarged sectional perspective view of the ultrasonic surgical instrument of FIG. 1 with the end effector in the open position and the shaft assembly in the first articulated configuration.
Figure 8A:
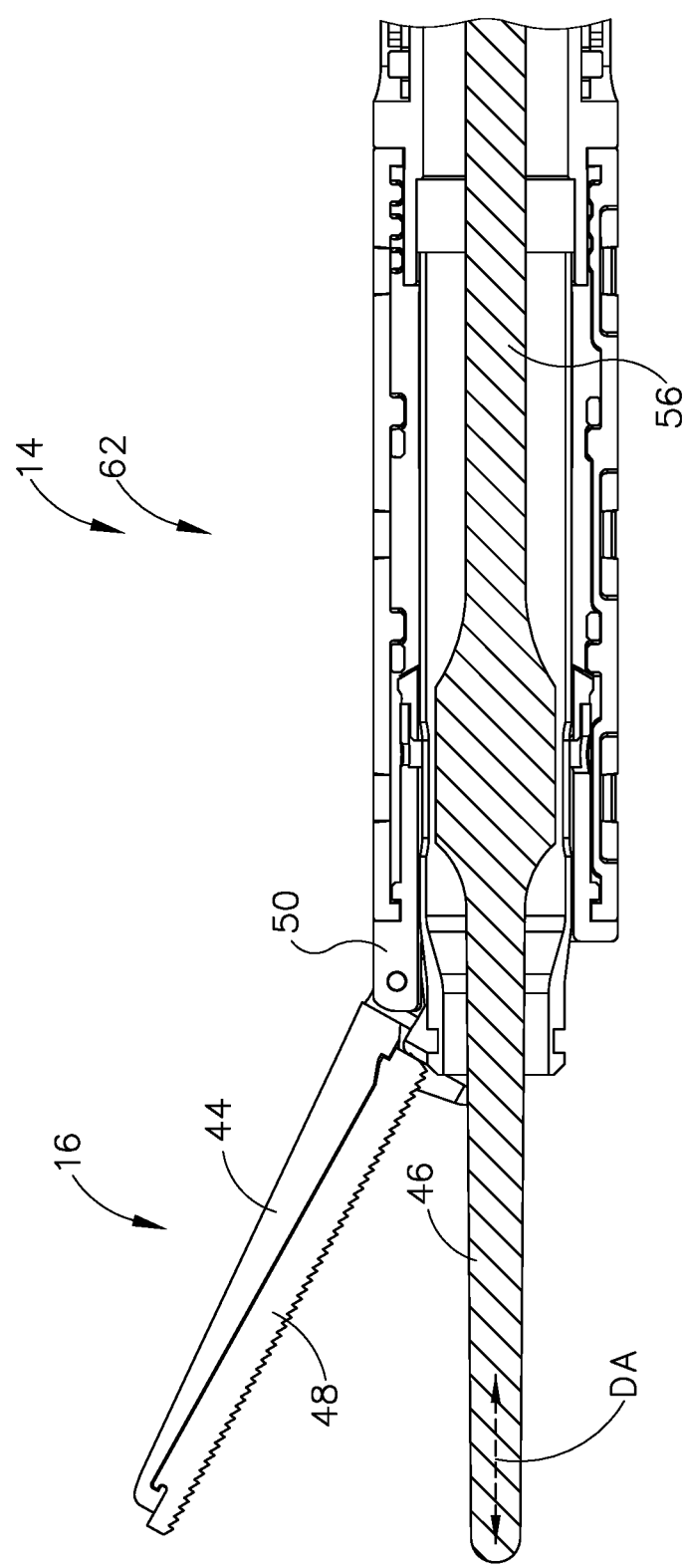
FIG. 8A depicts an enlarged cross-sectional view of the ultrasonic surgical instrument of FIG. 1 taken along a centerline thereof with the end effector in the open position and the shaft assembly in the non-articulated configuration.
Figure 8B:
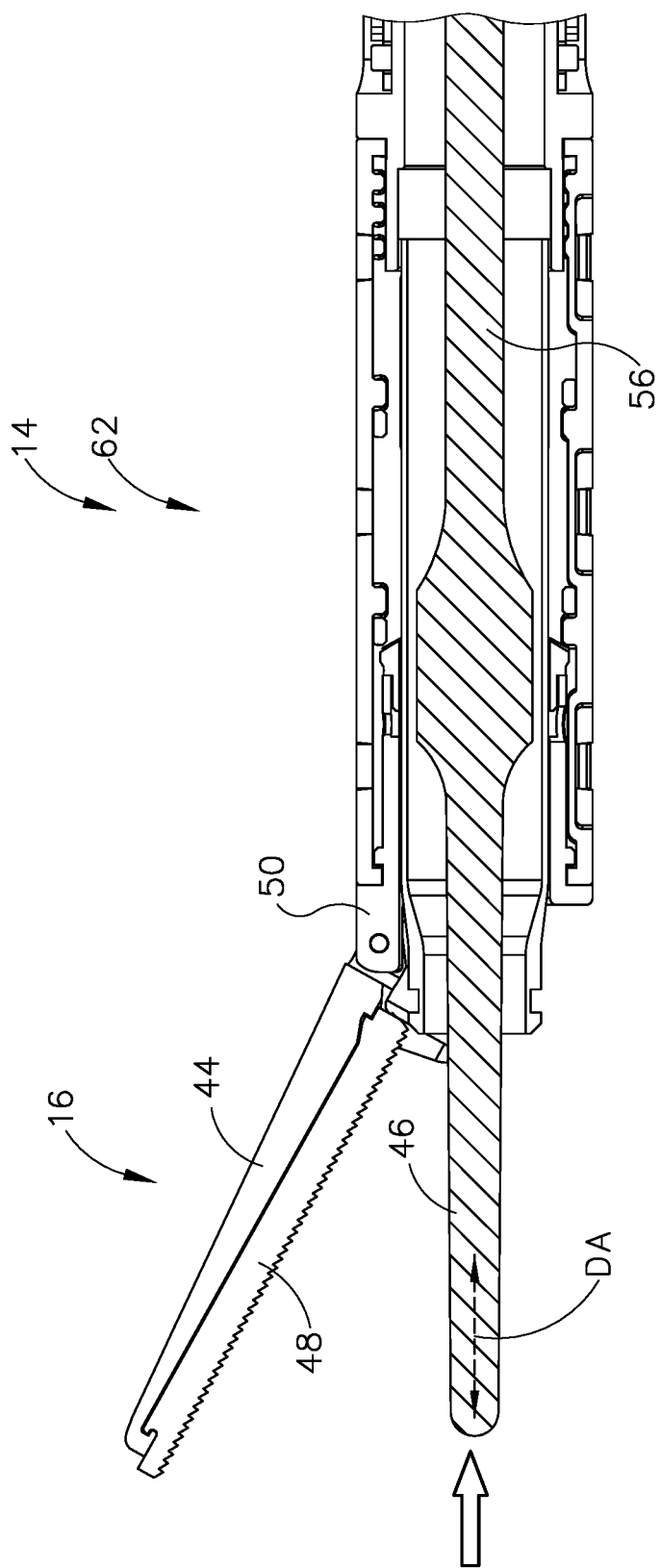
FIG. 8B depicts an enlarged cross-sectional view of the ultrasonic surgical instrument of FIG. 1 taken along a centerline thereof with the end effector in the open position and a shaft assembly in the first articulated configuration.

As mentioned above, end effector (16) is coupled to distal shaft portion (62), while distal shaft portion (62) is coupled with distal link (70) of articulation section (64). As also mentioned above, the distal ends of articulation bands (74) are coupled with distal link (70) such that opposing translation of articulation bands (74) causes articulation section (64) and flexible portion (58) of waveguide (56) to bend (see FIGS. 7A-7B), thereby laterally deflecting end effector (16) away from longitudinal axis (61). Waveguide (56) extends from transducer assembly (54) to blade (46) (see FIGS. 7A-8B) in order to transmit mechanical oscillations from transducer assembly (54) to blade (46) in accordance with the description herein. Therefore, blade (46) is coupled to a portion of waveguide (56) extending proximally from flexible portion (58) (see FIGS. 7A-7B).

Since clamp arm (44) deflects away from longitudinal axis (61) by following distal shaft portion (62), and since blade (46) deflects from longitudinal axis (61) by the bending of flexible portion (58) of waveguide (56), clamp arm (44) and blade (46) may deflect from longitudinal axis (61) along different arc lengths. In other words, the curve length which flexible portion (58) bends while articulation section (64) is in a first articulated configuration may be different than the curve length of the various elements that connect to and deflect clamp arm (44) while articulation section (64) is in the first articulated configuration. Therefore, the difference in respective arc lengths may result in a shift between blade (46) and clamp arm (44) along a distal axis (DA) (see FIGS. 8A-8B) while articulation section (64) is in an articulated configuration (see FIG. 8B) as compared to a non-articulated configuration (see FIG. 8A). Additionally, various other factors may also contribute to a shifting mismatch between blade (46) and clamp arm (44) relative to each other along distal axis (DA) between the articulated configuration (see FIG. 8B) and the non-articulated configuration (see FIG. 8A).

A. Exemplary Features to Accommodate Axial Shifting of Ultrasonic Blade

It may be desirable for shaft assembly (14) and end effector (16) to have features that accommodate for the above mentioned shift between blade (46) and clamp arm (44) such that blade (46) and clamp arm (44) are substantially aligned relative to each other along distal axis (DA) of distal shaft portion (62), regardless of the articulated configuration of shaft assembly (14). It should be understood that distal axis (DA) of distal shaft portion (62) may be substantially aligned with longitudinal axis (61) (see FIGS. 3A-4B) of proximal shaft portion (60) when shaft assembly (14) is in the non-articulated configuration. It should also be understood that distal axis (DA) of distal shaft portion (62) deflects relative to longitudinal axis (61) along with distal shaft portion (62) when shaft assembly (14) is in articulated configurations.

Figure 9A:
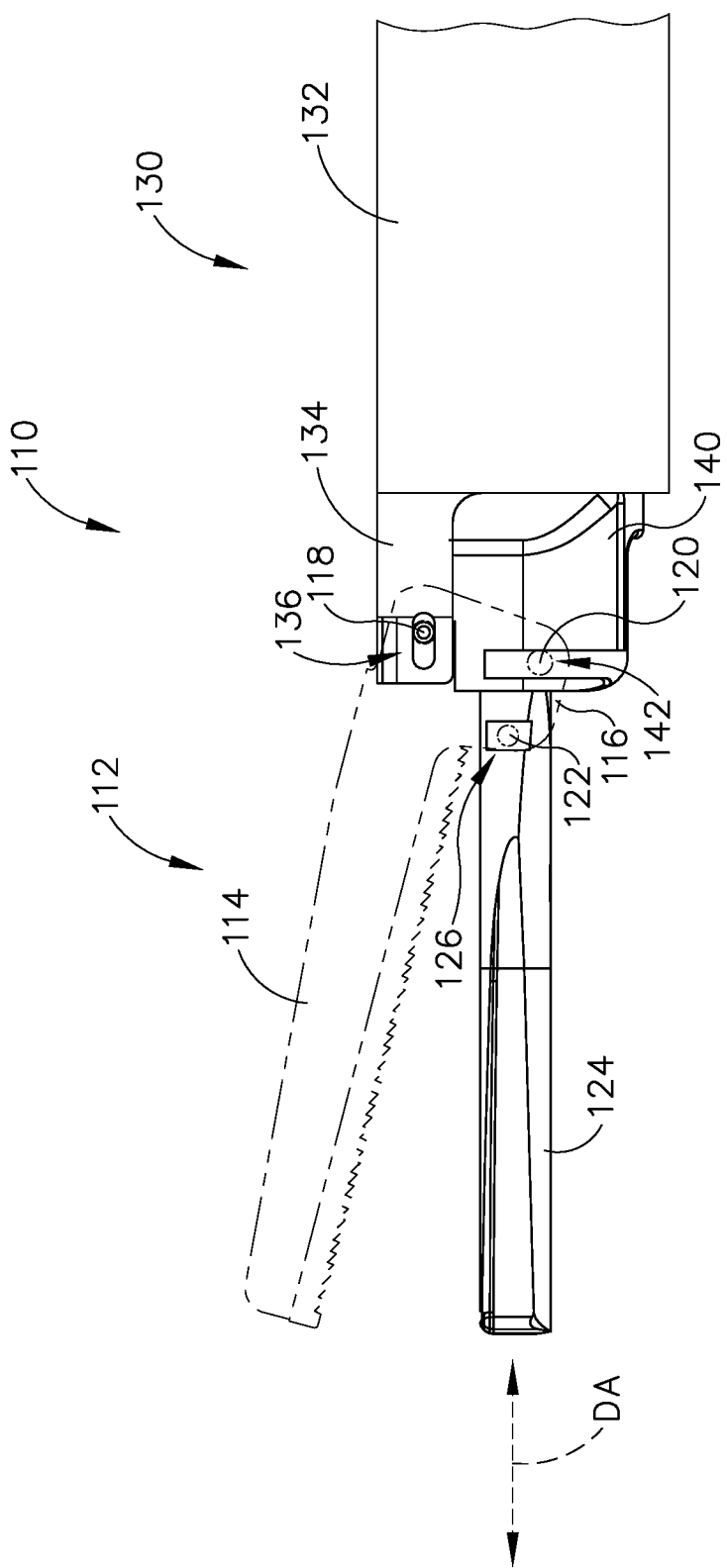
FIG. 9A depicts an elevational side view of a second ultrasonic surgical instrument, with an end effector in an open position and the shaft assembly in a non-articulated configuration.
Figure 9B:
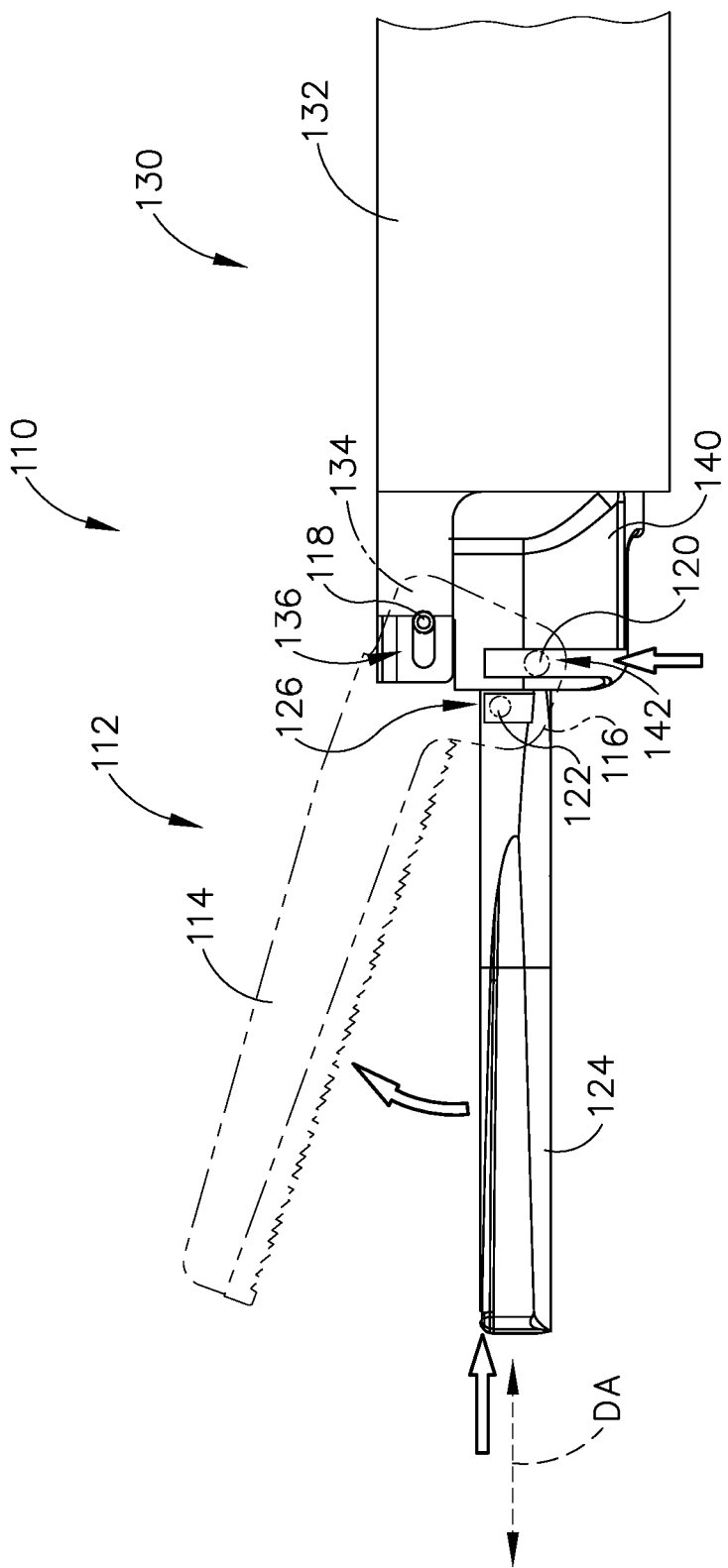
FIG. 9B depicts the elevational side view of the ultrasonic surgical instrument similar to FIG. 9A, but with the end effector in the open position and the shaft assembly in a first articulated configuration.
Figure 10:
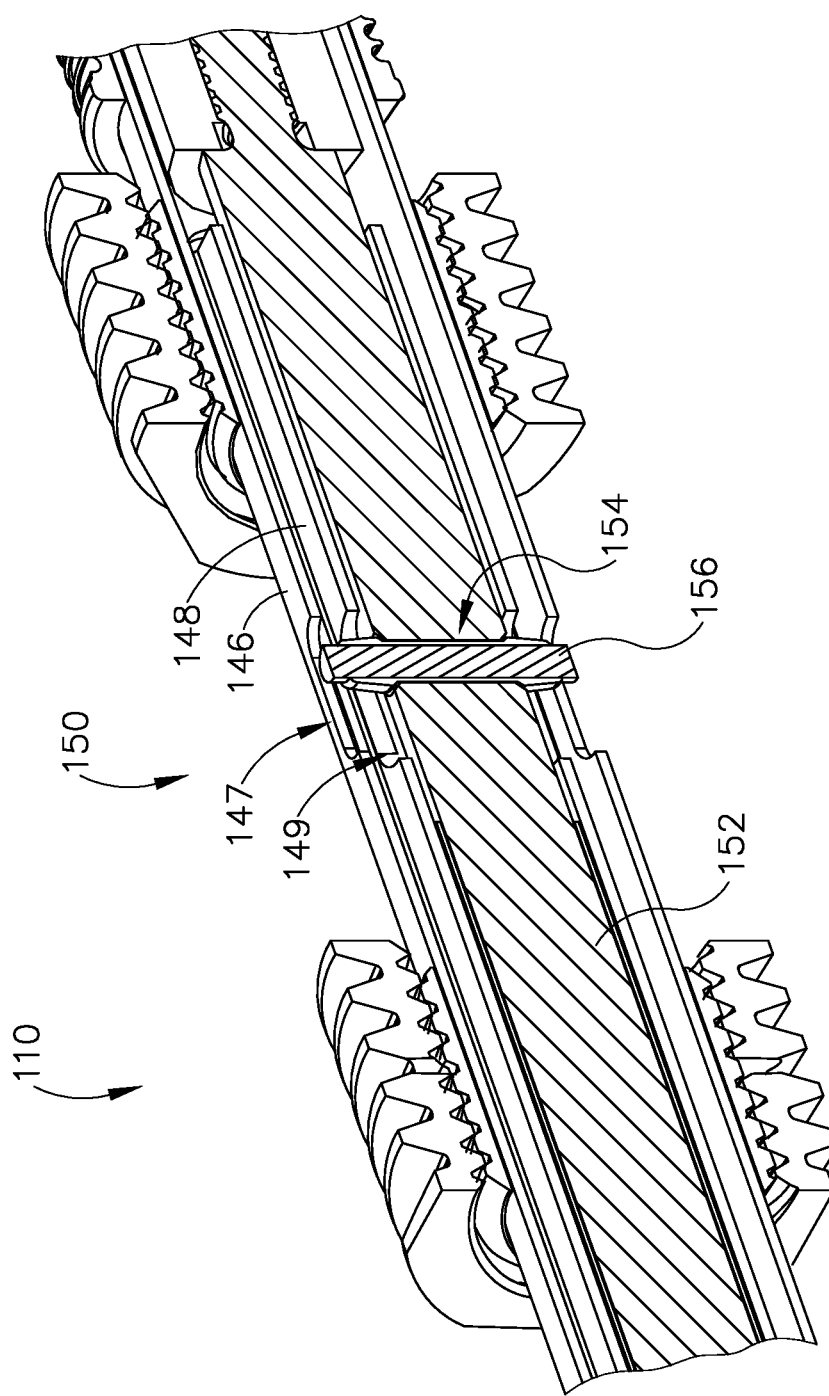
FIG. 10 depicts a sectional perspective view of a proximal end portion of the ultrasonic surgical instrument of FIG. 9A.

FIGS. 9A-10 show an exemplary second ultrasonic surgical instrument (110). In particular, FIGS. 9A-9B show an exemplary alternative end effector (112) and an alternative distal shaft portion (130) of ultrasonic surgical instrument (110) that may be readily incorporated into instrument (10) described above, in replacement of end effector (16) and distal shaft portion (62) described above, respectively. Additionally, FIG. 10 shows an exemplary alternative proximal shaft portion (150) of ultrasonic surgical instrument (110) that may be readily incorporated into instrument (10) described above in replacement of proximal shaft portion (60) described above.

End effector (112), distal shaft portion (130), and proximal shaft portion (150) may be substantially similar to end effector (16), distal shaft portion (62), and proximal shaft portion (60) described above, respectively, with differences elaborated below. As will be described in greater detail below, a clamp arm (114) of end effector (112) is configured to inhibit shifting relative to an ultrasonic blade (124) of end effector (112) along distal axis (DA) such that as end effector (112) is deflected relative to longitudinal axis (61) (see FIGS. 4A-4B), clamp arm (114) and ultrasonic blade (124) remain substantially aligned relative to each other along distal axis (DA).

Distal shaft portion (130) includes an outer shaft (132) and a translating clamp arm driver (140). A proximal end of outer shaft (132) may be coupled with distal link (70) (see FIG. 7A) of articulation section (64) (see FIG. 7A) such that distal shaft portion (130) and end effector (112) may be driven in similar positions as end effector (16) and distal shaft portion (62) descried above. In particular, FIG. 9A shows end effector (112) and distal shaft portion (130) in substantial alignment with longitudinal axis (61) (see FIGS. 3A-4B), similar to end effector (16) and distal shaft portion (62) shown in FIGS. 7A and 8A. Additionally, FIG. 9B shows end effector (112) and distal shaft portion (130) deflected from longitudinal axis (61) (see FIGS. 3A-4B), similar to end effector (16) and distal shaft portion (62) shown in FIGS. 7B and 8B.

Distal shaft portion (130) includes a distal tongue (134) that defines a locating slot (136). Locating slot (136) is dimensioned to pivotably couple with clamp arm (114) of end effector (112) such that clamp arm (114) may both pivot and translate relative to distal tongue (134) and outer shaft (132).

Translating clamp arm driver (140) defines a slot (142) that houses an inwardly presented protrusion (120) of clamp arm (114). Translating clamp arm driver (140) may extend proximally to couple with respective linear system actuator (36b, 36c, 36d, 36e, 36f) (see FIG. 5) such that respective linear system actuator (36b, 36c, 36d, 36e, 36f) (see FIG. 5) may actuate translating clamp arm driver (140) between a proximal position and a distal position. Actuation of translating clamp arm driver (140) between the proximal position and the distal position is configured to pivot clamp arm (114) between a closed position and an open position.

End effector (112) includes clamp arm (114) and ultrasonic blade (124), which may be substantially similar to clamp arm (44) and ultrasonic blade (46) described above, respectively, with differences elaborated below. While not shown, end effector (112) may include a clamp pad substantially similar to clamp pad (48) described above. Clamp arm (114) includes a pair of arms (116), pivot pin (118), and at least one inwardly presented protrusion (120), and a blade engagement protrusion (122).

Pivot pin (118) pivotably couples clamp arm (114) with a distal tongue (134) of outer shaft (132) about an axis defined by pivot pin (118), while inwardly presented protrusion (120) extends laterally inward from arms (116) into slot (142) defined by translating clamp arm driver (140). As mentioned above, translating clamp arm driver (140) is configured to actuate between a proximal position and a distal position. Since inwardly presented protrusion (120) is housed within slot (142), and since clamp arm (114) is further pivotably coupled to distal tongue (134) via pivot pin (118) and locating slot (136), actuation of translating clamp arm driver (140) drives clamp arm (114) to pivot about the axis defined by pivot pin (118) between the closed position and the open position (similar to clamp arm (44) shown in FIGS. 3A-3B). Inwardly presented protrusion (120) may travel along a path defined by slot (142) in response to pivoting of clamp arm (114).

Ultrasonic blade (124) extends proximally into an acoustic waveguide (152) (see FIG. 10). Acoustic waveguide (152) includes a flexible portion (not shown) that is substantially similar to flexible portion (58) of acoustic waveguide (56) (see FIGS. 7A-7B) described above. Therefore, ultrasonic blade (124) is configured to deflect relative to longitudinal axis (61) (see FIGS. 4A-4B) in a substantially similar manner as blade (46) described above.

Ultrasonic blade (124) defines a clamp arm locating slot (126) housing blade engagement protrusion (122) of clamp arm (114). As shown in FIGS. 9A-9B, blade engagement protrusion (122) is suitably housed within clamp arm locating slot (126) such that as blade (124) shifts relative to distal shaft portion (130) along distal axis (DA) in response to deflection of end effector (112) relative to longitudinal axis (61) (see FIGS. 4A-4B) between the position shown in FIG. 9A and the position shown in FIG. 9B, clamp arm (114) remains substantially aligned with blade (124) along distal axis (DA).

In particular, clamp arm locating slot (126) suitability engages blade engagement protrusion (122) such that as blade (124) shifts due to deflection of end effector (112) (see FIG. 9B), clamp arm locating slot (126) imparts an axial force onto clamp arm (114) via blade engagement protrusion (122), thereby translating clamp arm (114) relative to distal tongue (134) such that pivot pin (118) actuates within locating slot (136). Clamp arm (114) may actuate along with blade (124) in response to the shifting of blade (124) such that clamp arm (114) remains aligned with blade (124) along distal axis (DA), regardless of whether or not end effector (112) is deflected from longitudinal axis (61) (see FIGS. 4A-4B).

Clamp arm locating slot (126) may have any suitable geometry as would be apparent to one skilled in the art in view of the teachings herein. For example, clamp arm locating slot (126) may be dimensioned to suitably house blade engagement protrusion (122) while clamp arm (114) pivots between the closed position and the open position in accordance with the description herein. Thus, clamp arm locating slot (126) accommodates corresponding pivoting of blade engagement protrusion (122). In other words, clamp arm locating slot (126) and blade engagement protrusion (122) are dimensioned to suitably interact with each other to accommodate pivoting of clamp arm (114) between the closed and open positions, while still suitably functioning to align clamp arm (114) and blade (124) during the above mentioned shifting of blade (124).

Additionally, it should be understood that when translating clamp arm driver (140) translates between the proximal and distal position in order to pivot clamp arm (114) in accordance with the description herein, interaction between clamp arm locating slot (126) and blade engagement protrusion (122) may be sufficient to retain the longitudinal position of pivot pin (118) within locating slot (136) of distal tongue (134). In other words, pivoting of clamp arm (114) between the open and closed positions alone may not be enough force to translate pivot pin (118) within locating slot (136) defined by distal tongue (134).

In some instances, when blade (124) shifts in response to deflection of end effector (112) in accordance with the description above, a proximal portion of blade (124) may also shift. FIG. 10 shows proximal shaft portion (150) of ultrasonic surgical instrument (110). Proximal shaft portion (150) may be substantially similar to proximal shaft portion (60) described above, with differences elaborated below. Proximal shaft portion (150) includes a portion of acoustic waveguide (152) defining a proximal pin hole (154), an outer shaft (146) and an inner shaft (148). Proximal pin hole (154) of waveguide (152) is dimensioned to receive a pin (156) fixed within pin hole (154) when assembled. Both outer shaft (146) and inner shaft (148) define a respective longitudinal slot (147, 149) that slidably houses pin (156). Therefore, if a proximal portion of waveguide (152) shifts in accordance with the description herein, pin (156) may slide within slots (147, 149) without outer shaft (146) and inner shaft (148) interfering. Additionally, pin (156) and slots (147, 149) may interact to allow for waveguide (152) to remain rotationally fixed relative to outer shaft (146) and inner shaft (148) about longitudinal axis (61) (see FIGS. 4A-4B).

Figure 11A:
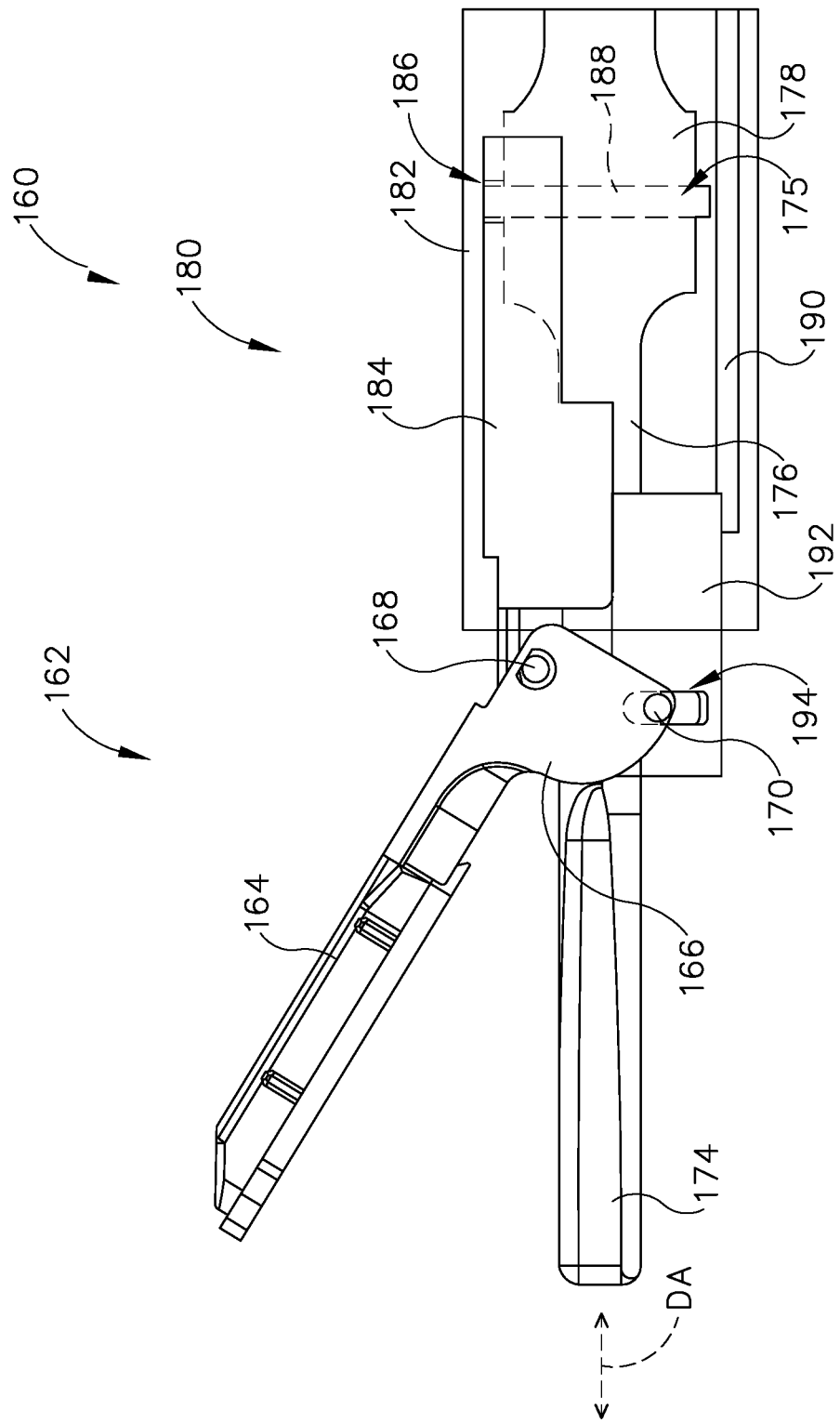
FIG. 11A depicts an elevational side view of a third ultrasonic surgical instrument, with an end effector in an open position and a shaft assembly in a non-articulated configuration.

FIGS. 11A-11B show an exemplary third ultrasonic surgical instrument (160) including an exemplary alternative end effector (162) and an alternative distal shaft portion (180) that may be readily incorporated into instrument (10) described above, in replacement of end effector (16) and distal shaft portion (62) described above, respectively.

End effector (162) and distal shaft portion (180) may be substantially similar to end effector (16) and distal shaft portion (62) described above, respectively, with differences elaborated below. As will be described in greater detail below, a clamp arm (164) of end effector (162) is configured to inhibit shifting relative to an ultrasonic blade (174) of end effector (162) along distal axis (DA) such that as end effector (162) is deflected relative to longitudinal axis (61) (see FIGS. 4A-4B), clamp arm (164) and ultrasonic blade (174) remain substantially aligned relative to each other along distal axis (DA).

Distal shaft portion (180) includes an outer shaft (182), a distal tongue (184), and a translating clamp arm driver (190). A proximal end of outer shaft (182) may be coupled with distal link (70) (see FIG. 7A) of articulation section (64) (see FIG. 7A) such that distal shaft portion (180) and end effector (162) may be driven in similar positions as end effector (16) and distal shaft portion (62) described above. In particular, FIG. 11A shows end effector (162) and distal shaft portion (180) in substantial alignment with longitudinal axis (61) (see FIGS. 3A-4B), similar to end effector (16) and distal shaft portion (62) shown in FIGS. 7A and 8A. Additionally, FIG. 11B shows end effector (162) and distal shaft portion (180) deflected from longitudinal axis (61) (see FIGS. 3A-4B), similar to end effector (16) and distal shaft portion (62) shown in FIGS. 7B and 8B.

Distal tongue (184) is slidably disposed within outer shaft (182). Distal tongue (184) is pivotably coupled with clamp arm (164) of end effector (162) such that clamp arm (164) may pivot between a closed position and an open position relative to distal tongue (184). Distal tongue (184) also defines a pin slot (186) dimensioned to receive a waveguide pin (188) that is fixed to an acoustic waveguide (176). As will be described in greater detail below, distal tongue (184) is coupled with waveguide (176) via waveguide pin (188) such that as blade (174) and waveguide (176) shift relative to outer shaft (182) in response to end effector (162) deflecting from longitudinal axis (61) (see FIGS. 4A-4B), distal tongue (184) and clamp arm (164) also correspondingly shift along with blade (174).

Translating clamp arm driver (190) includes a distal body (192) defining a slot (194) that houses an inwardly presented protrusion (170) of clamp arm (164). Translating clamp arm driver (190) may extend proximally to couple with respective linear system actuator (36b, 36c, 36d, 36e, 36f) (see FIG. 5) such that respective linear system actuator (36b, 36c, 36d, 36e, 36f) (see FIG. 5) may actuate translating clamp arm driver (190) between a proximal position and a distal position. Actuation of translating clamp arm driver (190) between the proximal position and the distal position is configured to pivot clamp arm (164) between a closed position and an open position.

End effector (162) includes clamp arm (164) and ultrasonic blade (174), which may be substantially similar to clamp arm (44) and ultrasonic blade (46) described above, respectively, with differences elaborated below. End effector (162) may include a clamp pad substantially similar to clamp pad (48) described above. Clamp arm (164) includes a pair of arms (166), pivot pin (168), and at least one inwardly presented protrusion (170).

Pivot pin (168) pivotably couples clamp arm (164) with distal tongue (184) about an axis defined by pivot pin (168), while inwardly presented protrusion (170) extends laterally inward from arms (166) into slot (194) defined by distal body (192) of translating clamp arm driver (190). As mentioned above, translating clamp arm driver (190) is configured to actuate between a proximal position and a distal position. Since inwardly presented protrusion (170) is housed within slot (194), and since clamp arm (164) is further pivotably coupled to distal tongue (184) via pivot pin (168), actuation of translating clamp arm driver (190) drives clamp arm (164) to pivot about the axis defined by pivot pin (168) between the closed position and the open position (similar to clamp arm (44) shown in FIGS. 3A-3B). Inwardly presented protrusion (170) may travel along a path defined by slot (194) in response to pivoting of clamp arm (164).

Ultrasonic blade (174) extends proximally into acoustic waveguide (176). Acoustic waveguide (176) includes a flexible portion (not shown) that is substantially similar to flexible portion (58) of acoustic waveguide (56) (see FIGS. 7A-7B) described above. Therefore, ultrasonic blade (174) is configured to deflect relative to longitudinal axis (61) (see FIGS. 4A-4B) in a substantially similar manner as blade (46) described above.

Additionally, acoustic waveguide (176) includes a distal flange (178) defining a pin hole (175) located at a corresponding nodal position. Distal flange (178) is located between flexible portion (not shown) and ultrasonic blade (174). A distal waveguide pin (188) extends through pin hole (175) and into pin slot (186) of distal tongue (184). Waveguide pin (188) is substantially fixed to acoustic waveguide (176) such that waveguide pin (188) rotates and translates with waveguide (176). Additionally, waveguide pin (188) is disposed within pin slot (186) of distal tongue (184) such that distal tongue (184) translates with waveguide pin (188) and waveguide (176).

Therefore, as shown in FIGS. 11A-11B, when blade (174) and waveguide (176) shift relative to outer shaft (182) due to deflection of end effector (162) (see FIG. 11B), waveguide pin (188) imparts an axial force onto distal tongue (184) via pin slot (186), thereby translating distal tongue (184) and clamp arm (164) relative to outer shaft (182) with waveguide (176) and blade (174). Therefore, clamp arm (164) may actuate along with blade (174) in response to the shifting of blade (174) such that clamp arm (164) remains aligned with blade (174) along distal axis (DA), regardless of whether or not end effector (162) is deflected from longitudinal axis (61) (see FIGS. 4A-4B).

Waveguide pin (188) may couple waveguide (176) with distal tongue (184) through any suitable means as would be apparent to one skilled in the art in view of the teachings herein. For example, a waveguide pin (188) may be a press pin or a threaded pin. Alternatively, instead of pin (188), distal tongue (184) may be coupled with waveguide (176) through any other suitable means as would be apparent to one skilled in the art in view of the teachings herein. For example, distal tongue (184) may be coupled with waveguide (176) via a threaded connection at distal flange (178).

As mentioned above, in some instances, clamp arm (44) may be configured to rotate in the direction as indicated by arrow (53) in FIG. 3A around ultrasonic blade (46). In such instances, it may be desirable to keep the functionality of rotating clamp arm (44) at least partially around ultrasonic blade (46) as indicated by arrow (53), while still maintaining features that promote alignment of clamp arm (44) with ultrasonic blade (46) along distal axis (DA) as ultrasonic blade (46) shifts in accordance with the description herein.

Figure 12:
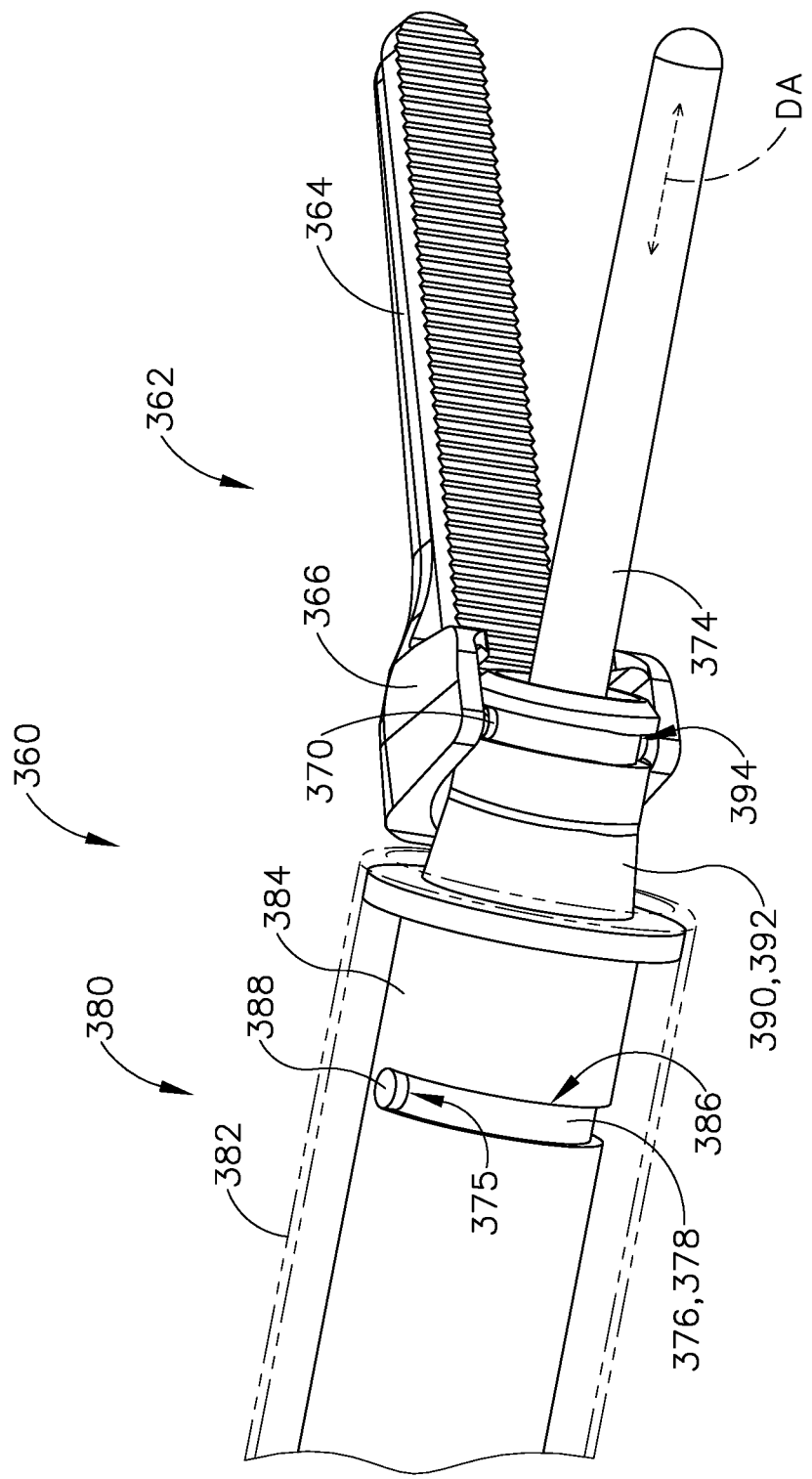
FIG. 12 depicts a perspective view of a fourth surgical instrument.
Figure 15:
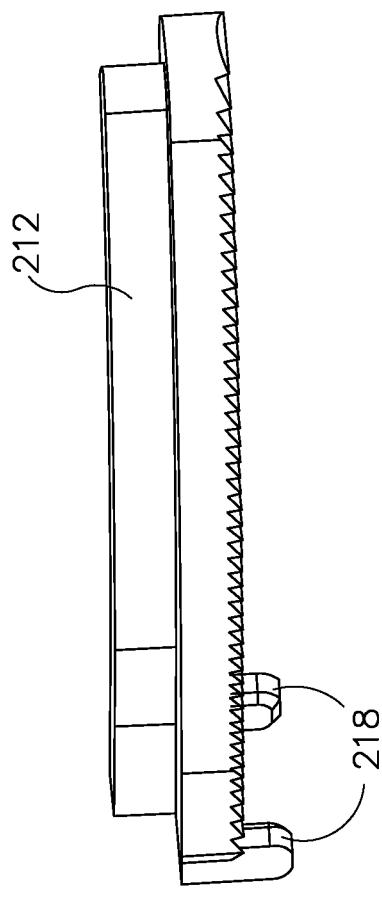
FIG. 15 depicts another perspective view of the clamp pad of FIG. 14.

FIG. 12 depicts an exemplary fourth ultrasonic surgical instrument (360) that is substantially similar to ultrasonic surgical instrument (160) described above, with differences elaborated below. Therefore, ultrasonic surgical instrument (360) includes end effector (362) and distal shaft portion (380), which are substantially similar to end effector (162) (see FIG. 11A) and distal shaft portion (180) (see FIG. 11A) described above, with differences elaborated below. In particular, instrument (360) is substantially similar to instrument (160) (see FIG. 11A) described above, except instrument (360) is also configured to accommodate for rotation of clamp arm (364) about ultrasonic blade (374) (i.e., clocking clamp arm (364) relative to ultrasonic blade (374) to various clocked positions) while maintaining the ability to promote alignment of clamp arm (364) with blade (374) along distal axis (DA) as blade (374) shifts in accordance with the description herein.

Therefore, end effector (362) includes clamp arm (364) and ultrasonic blade (374), which are substantially similar to clamp arm (164) (see FIG. 11A) and ultrasonic blade (174) (see FIG. 11A) described above, respectively, with differences elaborated below. Clamp arm (364) includes arms (366), a pivot pin (not shown), and at least one inwardly presented protrusion (370). Additionally, ultrasonic blade (374) extends proximally into an acoustic waveguide (376), which includes a distal flange (378) defining a pin hole (375) sized to receive a waveguide pin (388). Distal flange (378) is located between a flexible portion (not shown) and ultrasonic blade (374).

Distal shaft portion (380) includes outer shaft (382), distal tongue (384), and translating clamp arm driver (390). Translating clamp arm driver (390) includes a proximal body (392) configured to translate in order to pivot clamp arm (364) relative to distal tongue (384) and blade (374) between an open position and a closed position (similar to movement of clamp arm (44) as indicated by arrow (52) in FIGS. 3A-3B). Proximal body (392) defines an annular track (394) configured to suitably house inwardly presented protrusion (370) of clamp arm (364), regardless of the position clamp arm (364) is clocked around blade (374) (similar to rotation of clamp arm (44) about blade (46) as indicated by arrow (53) in FIG. 3A).

Clamp arm (364) is pivotably coupled with distal tongue (384) via pivot pin (not shown) such that clamp arm (364) may pivot relative to distal tongue (384) and blade (374) between the open position and the closed position. Distal tongue (384) is rotatably disposed about distal flange (378) such that distal tongue (384) may rotate clamp arm (364) about blade (374) into various clocked positions (similar to rotation of clamp arm (44) about blade (46) as indicated by arrow (53) in FIG. 3A); while clamp arm (364) also maintains the ability to pivot between the open position and the closed position, regardless of the clocked position of clamp arm (364) about blade (374). Any suitable driving mechanism may be used in order to drive rotation of distal tongue (384) about distal flange (378) of waveguide (376) as would be apparent to one skilled in the art in view of the teachings herein.

As mentioned above, instrument (360) is configured to accommodate clocking rotation of clamp arm (364) about ultrasonic blade (374) (similar to rotation of clamp arm (44) about blade (46) as indicated by arrow (53) in FIG. 3A), while maintaining the ability to promote alignment of clamp arm (364) with blade (374) along distal axis (DA) as blade (374) shifts in accordance with the description herein. In particular, distal tongue (384) defines a circumferential pin slot (386) that houses waveguide pin (388) to allow distal tongue (384) to rotate about waveguide (376) such that waveguide pin (388) travels along the path defined by circumferential pin slot (386). Therefore, clamp arm (364) may also rotate about ultrasonic blade (374) into various clocked positions in accordance with the description herein (similar to rotation of clamp arm (44) about blade (46) as indicated by arrow (53) in FIG. 3A). While circumferential pin slot (386) is dimensioned to accommodate for waveguide pin (388) to rotate along the path defined by circumferential pin slot (386), circumferential pin slot (386) may still abut against waveguide pin (388) as blade (374) shifts relative to outer shaft (382) in a direction along distal axis (DA) in accordance with the description herein. Therefore, clamp arm (364) may still align with blade (374) along distal axis (DA) in response to blade (374) shifting as waveguide pin (388) abuts against circumferential pin slot (386) of distal tongue (384); while clamp arm (364) may also rotate around ultrasonic blade (374) into various clocked positions.

B. Exemplary Features to Accommodate Rotational Misalignment of Ultrasonic Blade and Clamp Arm In some instances, clamp arm (44) or blade (46) may inadvertently rotate relative to each other in the direction as indicated by arrow (53) (see FIG. 3A) (i.e. clock) into an undesirable clocked position such that as clamp arm (44) pivots relative to blade (46). For instance, blade (46) may inadvertently clock into an undesirable position relative to clamp arm (44) in response to deflecting from longitudinal axis (61) (see FIGS. 4A-4B). Therefore, it may be desirable to have an alignment feature to align clamp arm (44) into the desired clocked position relative to blade (46) as clamp arm (44) pivots from the open position to the closed position (as shown in FIGS. 3B-3A).

FIG. 13 shows an exemplary fifth ultrasonic surgical instrument (200). Ultrasonic surgical instrument (200) includes an end effector (202) and a distal shaft portion (205), which may be readily incorporated into instrument (10) described above in replacement of end effector (16) and distal shaft portion (62) described above. End effector (202) includes a clamp arm (204), a clamp pad (212), and an ultrasonic blade (214). Clamp arm (204) and clamp pad (212) are pivotably coupled between an open position and a closed position via pivot pin (208). Clamp arm (204) includes arms (206) having an inwardly presented projection (210) suitably coupled with a translating clamp arm driver (209) of distal shaft portion (205). Distal shaft portion (205) includes a distal tongue (207) which clamp arm (204) and clamp pad (212) are pivotably connected to via pivot pin (208). Translating clamp arm driver (209) is configured to translate in order to pivot clamp arm (204) and clamp pad (212) about pivot pin (208) between the open and closed positions.

Clamp pad (212) include a pair of blade engagement arms (218) dimensioned to abut against a pair flats (216) of ultrasonic blade (214) as clamp arm (204) and clamp pad (212) pivot from the open position to the closed position. Contact between blade engagement arms (218) and flats (216) may suitably align clamp pad (212) relative to blade (214) in a desired clocked position as clamp pad (212) is pivoted toward the closed position. Therefore, as clamp pad (212) and blade (214) are misaligned prior to clamp pad (212) transitioning to the closed position, contact between engagement arms (218) and flats (216) may force clamp pad (212) and blade (214) into the suitably clocked position.

Figure 16:
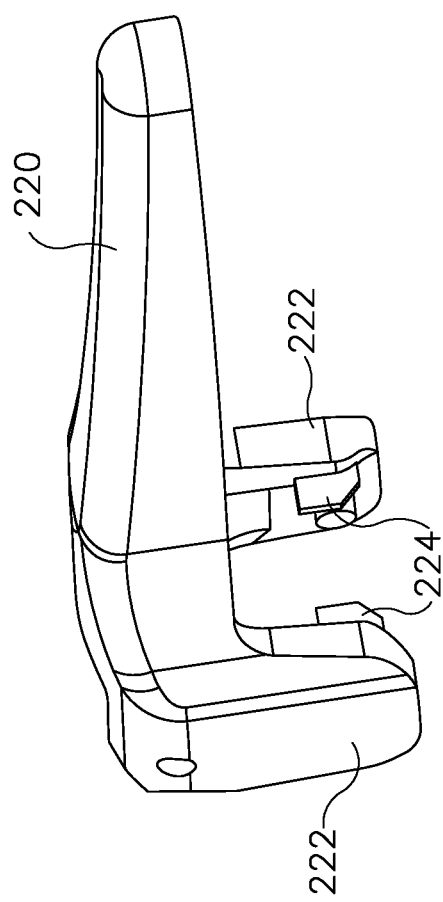
FIG. 16 depicts a perspective view of an alternative clamp arm that may be readily incorporated into the ultrasonic surgical instrument of FIG. 13.

In some instances, blade engagement arms (218) may be made of a different material compared to a remainder of clamp pad (212). In some instances, blade engagement arms (218) may be fixed to clamp arm (204) rather than clamp pad (212). An example of this is shown in FIG. 16 in which an alternative clamp arm (220) includes arms (222) having blade engagement arms (224) extending laterally inward. Blade engagement arms (224) may operate substantially similarly to blade engagement arms (218) described above, except blade engagement arms (224) are fixed to clamp arm (220), instead of a clamp pad.

III. Exemplary Acoustic Waveguide with Various Distal Flanges

As mentioned above, in some instances, acoustic waveguide (176, 376) includes distal flange (178, 378) located between flexible portion (not shown) of waveguide (176, 376) and ultrasonic blade (174, 374). Distal flange (178, 378) may be generally located at a nodal position. Proper design of distal flange (178, 378) and constraint of distal flange (178, 378) within distal shaft portion (180, 380) may allow for deflection of blade (174, 374) away from longitudinal axis (61) as indicated by arrow (66) (see FIG. 3A). Without consideration of distal flange (178, 378) constraint, instrument (160, 360) may suffer from poor blade (174, 374) to clamp arm (164, 364) alignment, significant tip dive, high ultrasonic impedance and high clamping resistance. As a result, instrument (160, 360) would experience poor or inconsistent pressure profiles, undesired tip motion, additional heat generation, and high clamp loads. Therefore, it may be desirable to create a robust distal flange constraint which improves the overall performance of instrument (160, 360). It should be understood that the various features of distal flanges described below may be combined to provide for the various functions listed below.

FIGS. 17-18 show an alternative acoustic waveguide (230) and ultrasonic blade (232) that may be readily incorporated into instrument (10, 110, 160, 200) described above. Waveguide (230) includes a distal flange (235) located between flexible portion (not shown) and ultrasonic blade (232). Distal flange (235) may be generally located at a nodal position. Distal flange (235) includes opposing arched surfaces (234) and opposing flat surfaces (236). Flat surfaces (236) may be machined from distal flange (235). Flat surfaces (236) may be held into distal shaft portion (180, 380) by overmolds or other mechanisms that would be apparent to one skilled in the art in view of the teachings herein. Flat surfaces (236) may reduce rotational and transverse misalignment of blade (232) when flexible section (not shown) is bent.

Figure 19:
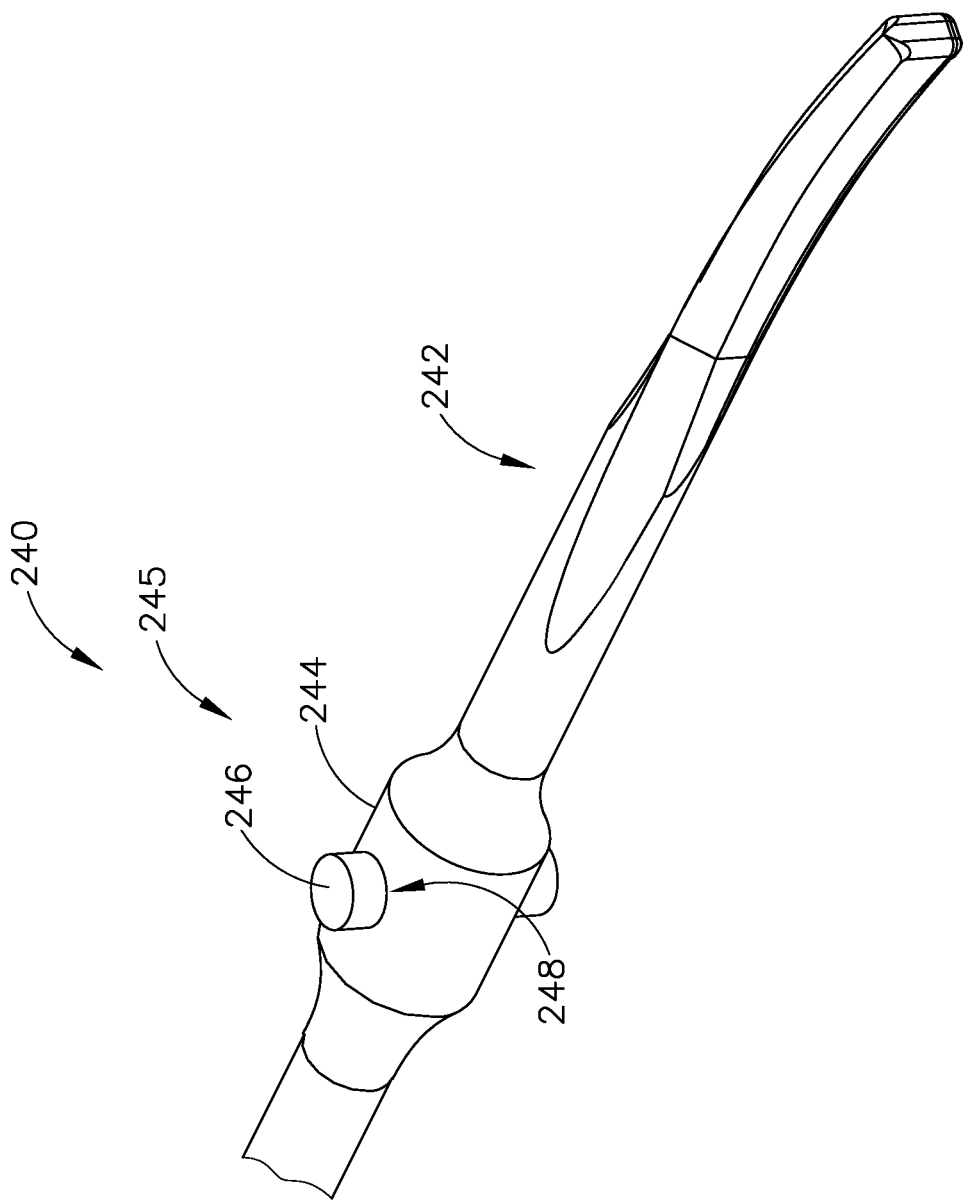
FIG. 19 depicts a perspective view of a second exemplar of a flanged acoustic waveguide and an ultrasonic blade that may be readily incorporated into the ultrasonic surgical instrument of FIG. 1.

FIG. 19 shows an alternative acoustic waveguide (240) and ultrasonic blade (242) that may be readily incorporated into instrument (10, 110, 160, 200) described above. Waveguide (240) includes a distal flange (245) located between flexible portion (not shown) and ultrasonic blade (242). Distal flange (245) may be generally located at a nodal position. Distal flange (245) includes an arched surface (244) defining a threaded pin hole (248) and a threaded pin (246) coupled with arched surface (244) via threaded pin hole (248). Threaded pin hole (248) may be machined into arched surface (244) and threaded pin (246) may be screwed into threaded pin hole (248). Threaded pin (246) and threaded pin hole (248) may reduce axial, rotational, and transverse misalignment of blade (242) when flexible section (not shown) is bent. In some instances, no threads are used to connect pin (246) with arched surfaces (244).

Figure 20:
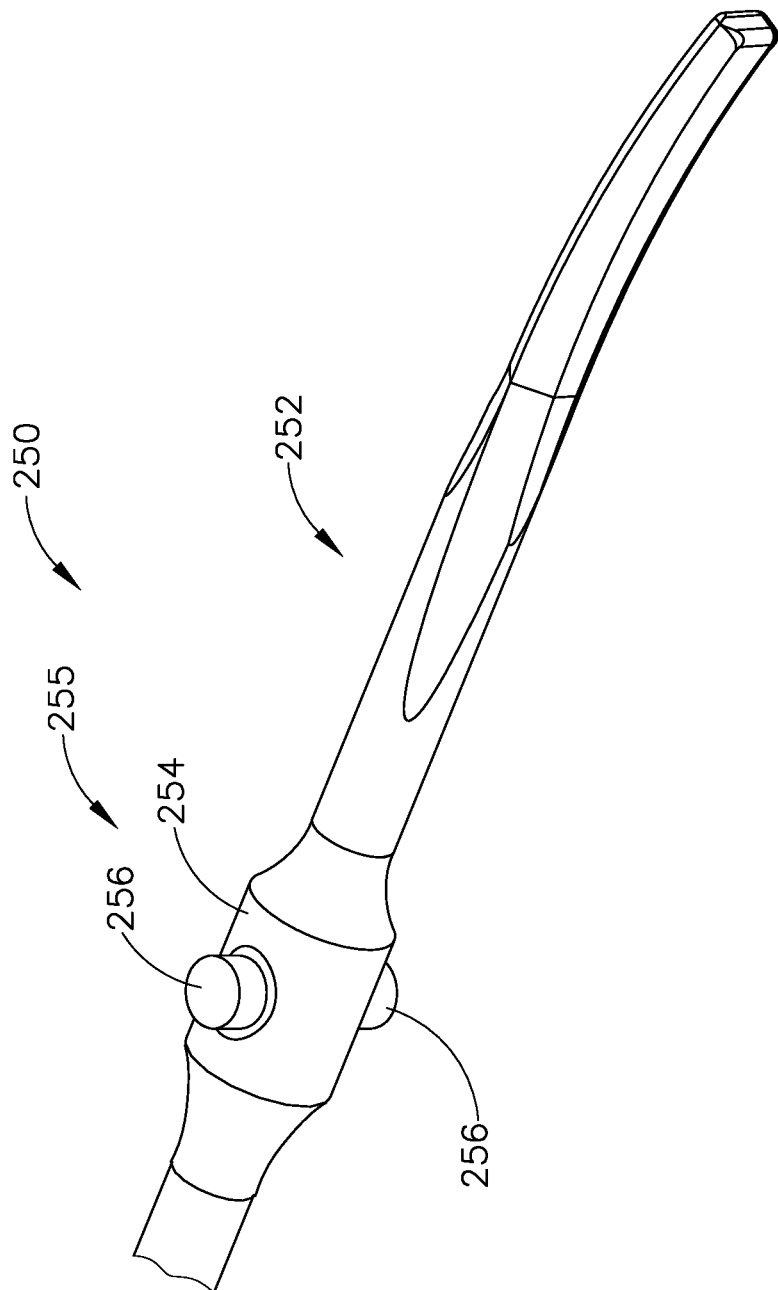
FIG. 20 depicts a perspective view of a third example of a flanged acoustic waveguide and an ultrasonic blade that may be readily incorporated into the ultrasonic surgical instrument of FIG. 1.

FIG. 20 shows an alternative acoustic waveguide (250) and ultrasonic blade (252) that may be readily incorporated into instrument (10, 110, 160, 200) described above. Waveguide (250) includes a distal flange (255) located between flexible portion (not shown) and ultrasonic blade (252). Distal flange (255) may be generally located at a nodal position. Distal flange (255) includes an arched surface (254) and a boss (256) extending from arched surface (254). Boss (256) may be machined from distal flange (255). Boss (256) may be coupled to distal shaft portion (180, 380) by overmolds or other mechanisms that would be apparent to one skilled in the art in view of the teachings herein. Boss (256) may reduce axial, rotational, and transverse misalignment of blade (242) when flexible section (not shown) is bent.

FIGS. 21-22 show an alternative acoustic waveguide (260) and ultrasonic blade (262) that may be readily incorporated into instrument (10, 110, 160, 200) described above. Waveguide (260) includes a distal flange (265) located between flexible portion (not shown) and ultrasonic blade (262). Distal flange (265) may be generally located at a nodal position. Distal flange (265) includes a threaded waveguide portion (266) and a threaded overmold portion (268). Threaded waveguide portion (266) may be machined onto waveguide (260) and threaded overmold portion (268) may be screwed onto threaded waveguide portion (266). Threaded overmold portion (268) may be formed of any suitable material that would be apparent to one skilled in the art in view of the teachings herein. For instance, threaded overmold portion (268) may be formed from plastic. Threaded overmold portion (268) may reduce transverse misalignment and increases clamping stiffness. Threaded overmold portion (268) may also allow for a translating body to encompass and translate axially over overmold portion (268), such that translating body may open and close a clamp arm assembly.

Figure 24:
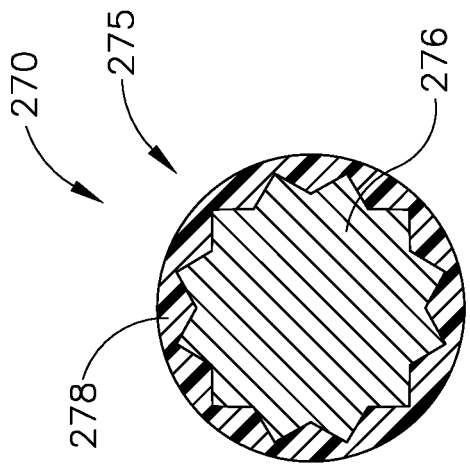
FIG. 24 depicts a cross-sectional view of the acoustic waveguide of FIG. 23, taken along sectional line 24-24 of FIG. 23.
Figure 23:
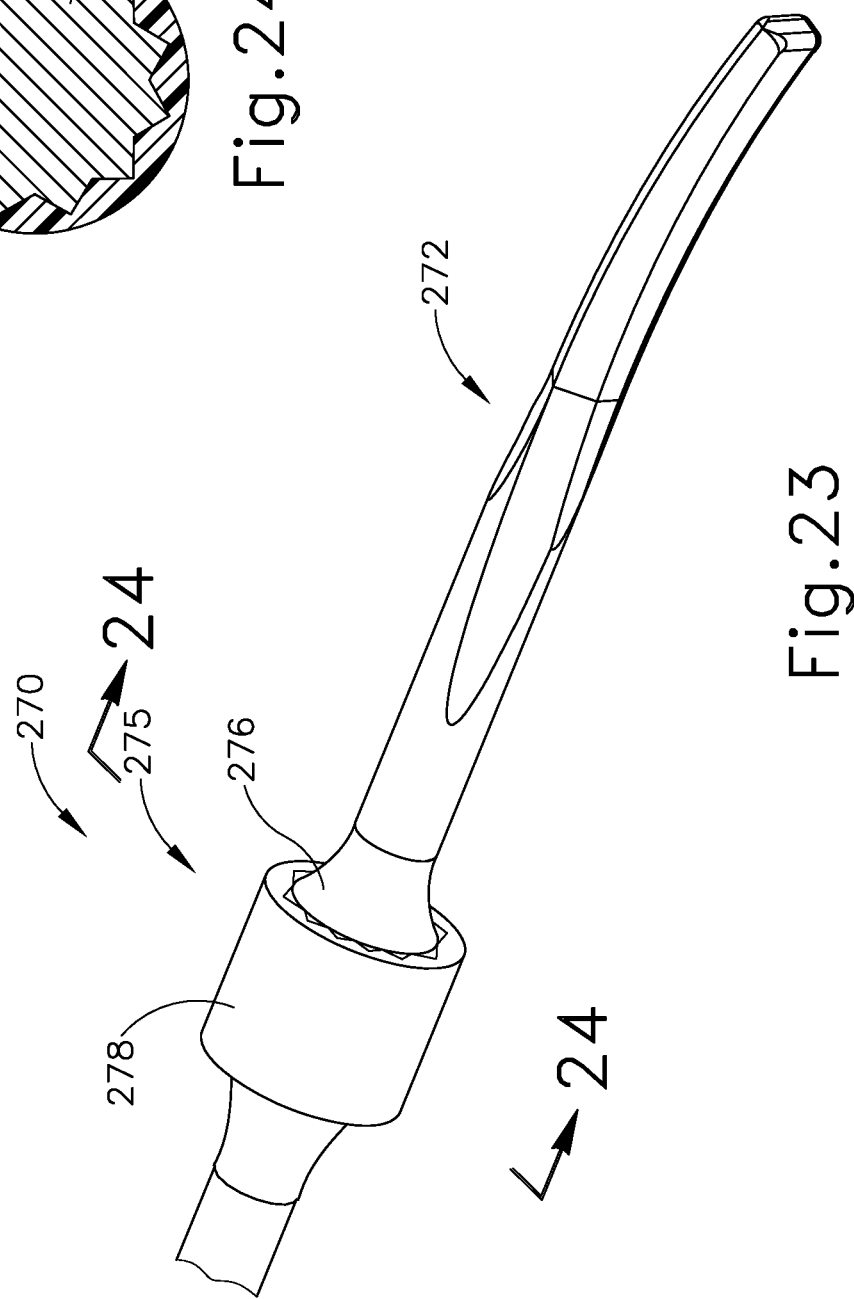
FIG. 23 depicts a perspective view of a fifth example of a flanged acoustic waveguide and an ultrasonic blade that may be readily incorporated into the ultrasonic surgical instrument of FIG. 1.

FIGS. 23-24 show an alternative acoustic waveguide (270) and ultrasonic blade (272) that may be readily incorporated into instrument (10, 110, 160, 200) described above. Waveguide (270) includes a distal flange (275) located between flexible portion (not shown) and ultrasonic blade (272). Distal flange (275) may be generally located at a nodal position. Distal flange (275) includes a splined waveguide portion (276) and a splined overmold portion (278). Splined waveguide portion (276) may be machined onto waveguide (270) and splined overmold portion (278) may be slide onto splined waveguide portion (276). Splined overmold portion (278) may be formed of any suitable material that would be apparent to one skilled in the art in view of the teachings herein. For instance, splined overmold portion (278) may be formed from plastic. Splined overmold portion (278) may reduce transverse misalignment and increase clamping stiffness. Splined overmold portion (278) may also allow for a translating body to encompass and translate axially over overmold portion (278), such that translating body may open and close a clamp arm assembly.

Figure 26:
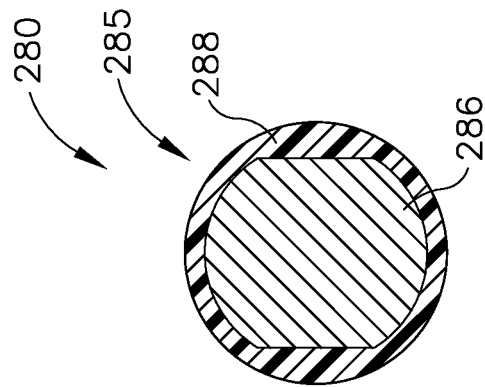
FIG. 26 depicts a cross-sectional view of the acoustic waveguide of FIG. 25, taken along sectional line 26-26 of FIG. 25.
Figure 25:
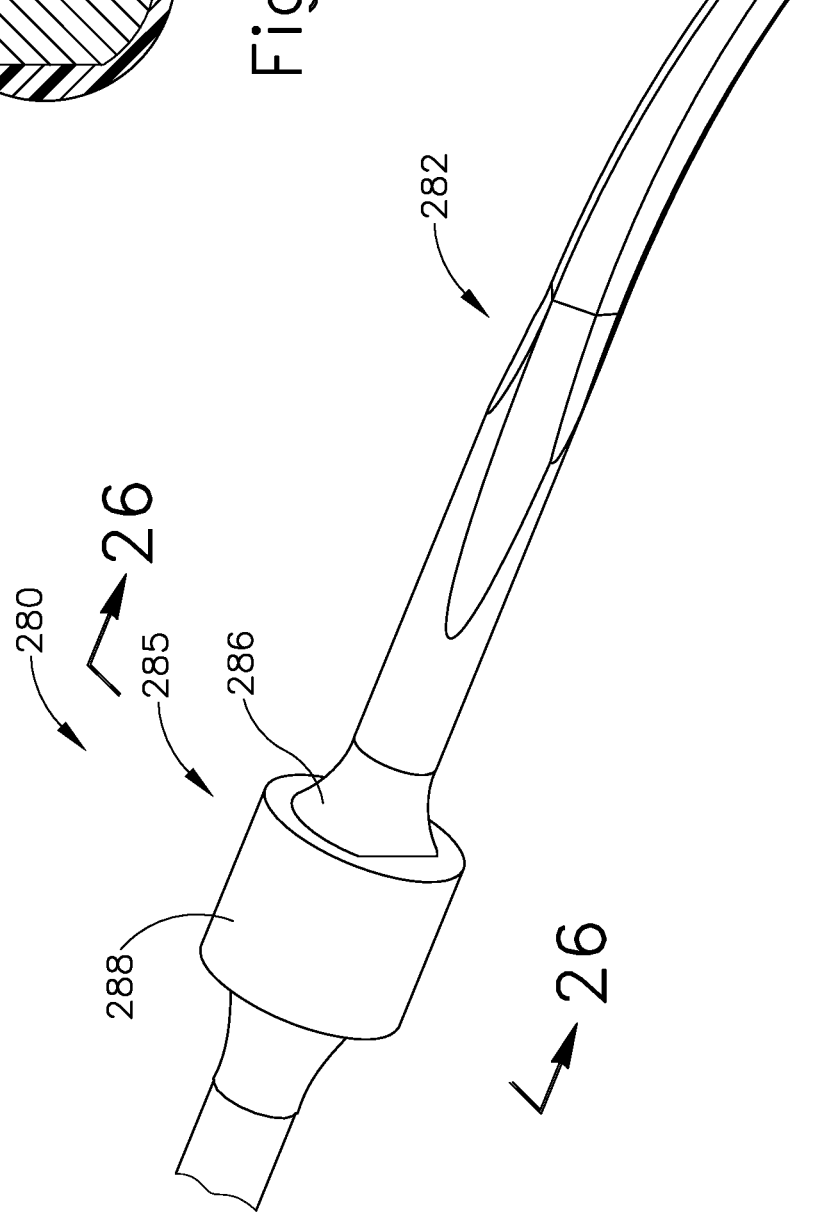
FIG. 25 depicts a perspective view of a sixth example of a flanged acoustic waveguide and an ultrasonic blade that may be readily incorporated into the ultrasonic surgical instrument of FIG. 1.

FIGS. 25-26 show an alternative acoustic waveguide (280) and ultrasonic blade (282) that may be readily incorporated into instrument (10, 110, 160, 200) described above. Waveguide (280) includes a distal flange (285) located between flexible portion (not shown) and ultrasonic blade (282). Distal flange (285) may be generally located at a nodal position. Distal flange (285) includes a flattened waveguide portion (286) and a flattened overmold portion (288). Flattened waveguide portion (286) may be machined onto waveguide (280) and flattened overmold portion (288) may be slide onto flattened waveguide portion (286). Flattened overmold portion (288) may be formed of any suitable material that would be apparent to one skilled in the art in view of the teachings herein. For instance, flattened overmold portion (288) may be formed from plastic. Flattened overmold portion (288) may reduce transverse misalignment and increase clamping stiffness. Flattened overmold portion (288) may also allow for a translating body to encompass and translate axially over overmold portion (288), such that translating body may open and close a clamp arm assembly.

Figure 27:
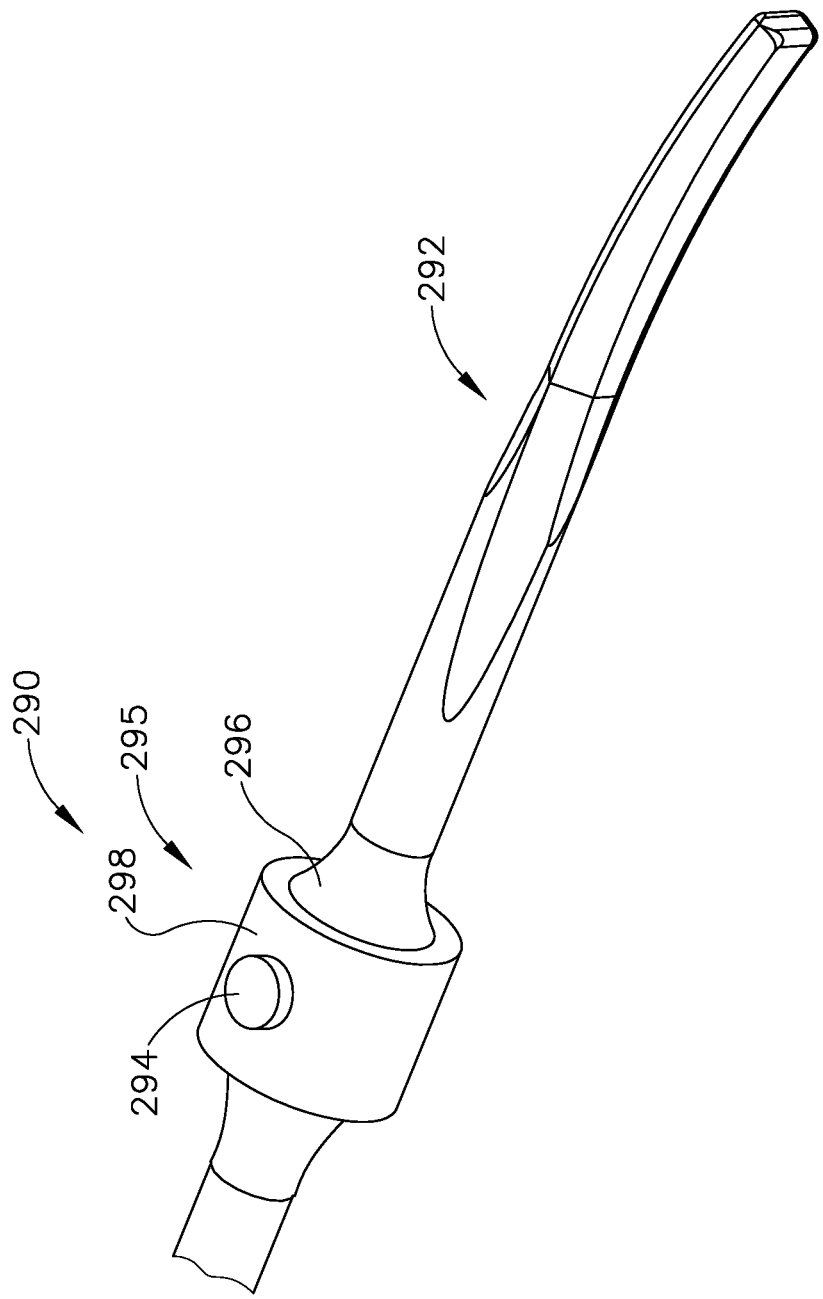
FIG. 27 depicts a perspective view of an alternative acoustic waveguide and an ultrasonic blade that may be readily incorporated into the ultrasonic surgical instrument of FIG. 1.

FIG. 27 shows an alternative acoustic waveguide (290) and ultrasonic blade (292) that may be readily incorporated into instrument (10, 110, 160, 200) described above. Waveguide (290) includes a distal flange (295) located between flexible portion (not shown) and ultrasonic blade (292). Distal flange (295) may be generally located at a nodal position. Distal flange (295) includes a waveguide flange portion (296) and an overmold flange portion (298) including a boss (294). Boss (294) may be machined on overmold flange portion (298). Overmold flange portion (298) may be formed of any suitable material that would be apparent to one skilled in the art in view of the teachings herein. For instance, overmold flange portion (298) may be formed from plastic. Overmold flange portion (298) may reduce axial and rotational misalignment of blade (292) when flexible section (not shown) is bent.

Figure 29:
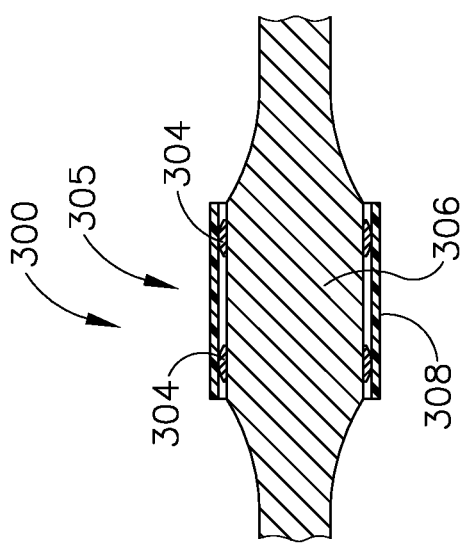
FIG. 29 depicts a cross-sectional view of the acoustic waveguide of FIG. 28, taken along sectional line 29-29 of FIG. 28.
Figure 28:
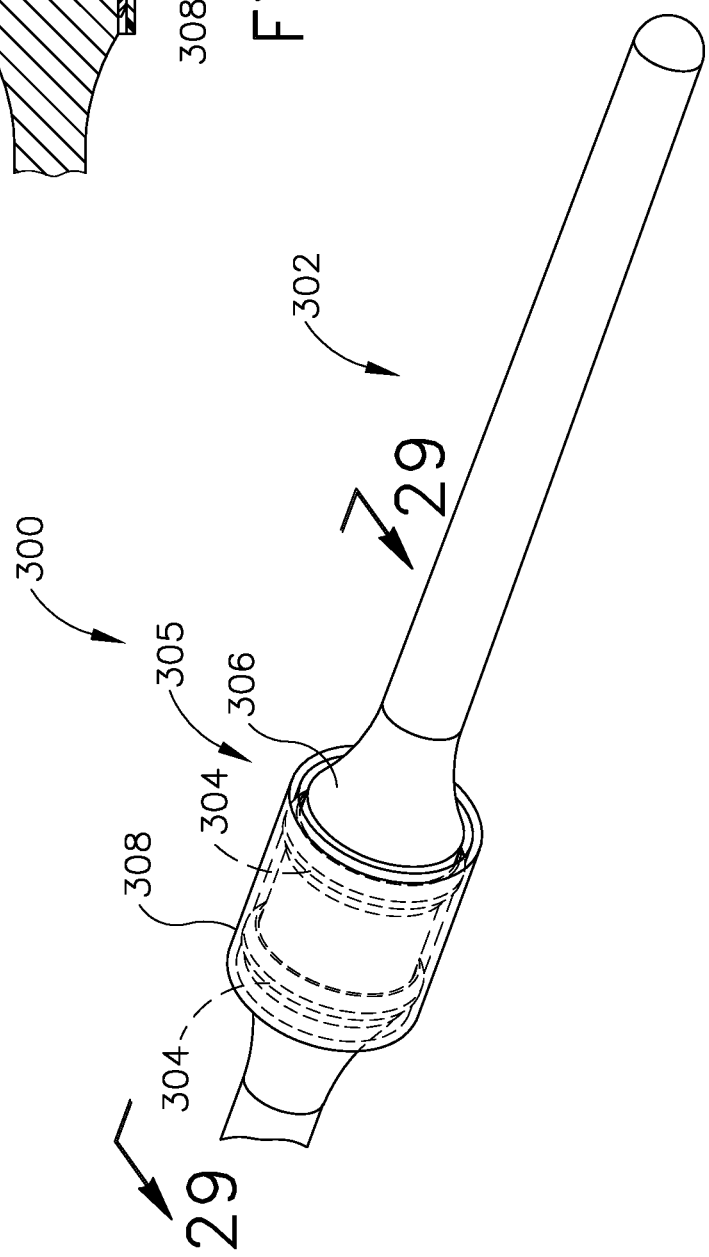
FIG. 28 depicts a perspective view of an alternative acoustic waveguide and an ultrasonic blade that may be readily incorporated into the ultrasonic surgical instrument of FIG. 1.

FIGS. 28-29 show an alternative acoustic waveguide (300) and ultrasonic blade (302) that may be readily incorporated into instrument (10, 110, 160, 200) described above. Waveguide (300) includes a distal flange (305) located between flexible portion (not shown) and ultrasonic blade (302). Distal flange (305) may be generally located at a nodal position. Distal flange (305) includes a waveguide flange portion (306), a compression sleeve (308), and a pair of overmold rings (304) surrounding waveguide flange portion (306) and interposed between waveguide flange portion (306) and compression sleeve (308). Overmold rings (304) may be formed from any suitable material as would be apparent to one skilled in the art in view of the teachings herein. For instance, overmold rings (304) may be formed from a silicone material. Compression sleeve (308) is placed over overmold rings (304) to place overmold rings (304) in compression between compression sleeve (308) and waveguide flange portion (306). This compression may reduce transverse misalignment, increase clamping stiffness, and minimize ultrasonic impedance. Compression sleeve (308) may also allow for a translating body to encompass and translate axially over compression sleeve (308), such that translating body may open and close a clamp arm assembly.

Figure 31:
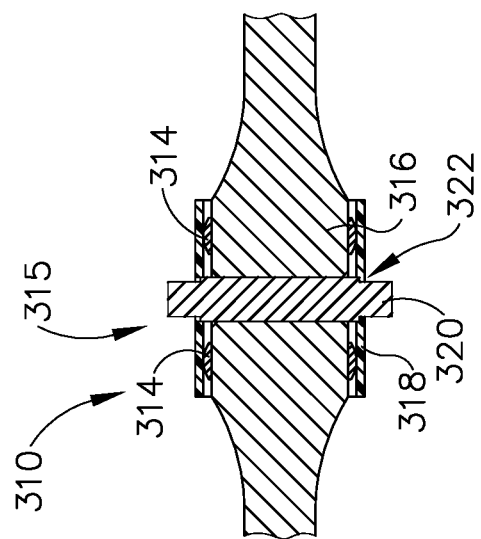
FIG. 31 depicts a cross-sectional view of the acoustic waveguide of FIG. 30, taken along sectional line 31-31 of FIG. 30.
Figure 30:
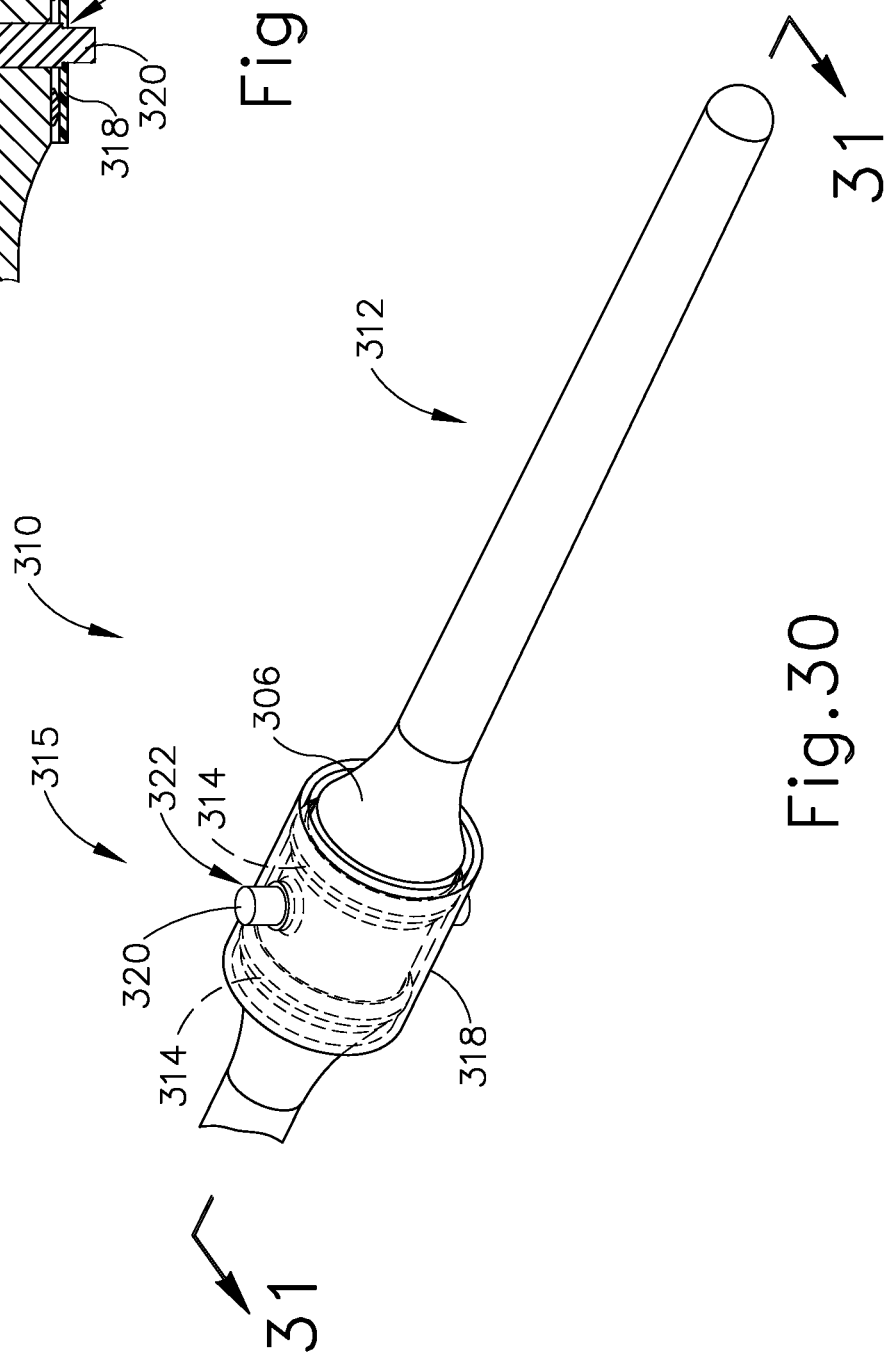
FIG. 30 depicts a perspective view of an alternative acoustic waveguide and an ultrasonic blade that may be readily incorporated into the ultrasonic surgical instrument of FIG. 1.

FIGS. 30-31 show an alternative acoustic waveguide (310) and ultrasonic blade (312) that may be readily incorporated into instrument (10, 110, 160, 200) described above. Waveguide (310) includes a distal flange (315) located between flexible portion (not shown) and ultrasonic blade (312). Distal flange (315) may be generally located at a nodal position. Distal flange (315) includes a waveguide flange portion (316), a compression sleeve (318), and a pair of overmold rings (314) surrounding waveguide flange portion (316) and interposed between waveguide flange portion (316) and compression sleeve (318). Additionally, a waveguide pin (320) extends through sleeve (308) and waveguide flange portion (316). Overmold rings (314) may be formed from any suitable material as would be apparent to one skilled in the art in view of the teachings herein. For instance, overmold rings (314) may be formed from a silicone material. Compression sleeve (318) is placed over overmold rings (314) to place overmold rings (314) in compression between compression sleeve (318) and waveguide flange portion (316). This compression may reduce transverse misalignment, increase clamping stiffness, and minimize ultrasonic impedance. Compression sleeve (318) may also allow for a translating body to encompass and translate axially over compression sleeve (318), such that translating body may open and close a clamp arm assembly. The addition on pin (320) may provide for the various advantages mentioned above relative to pins or bosses.

Figure 32:
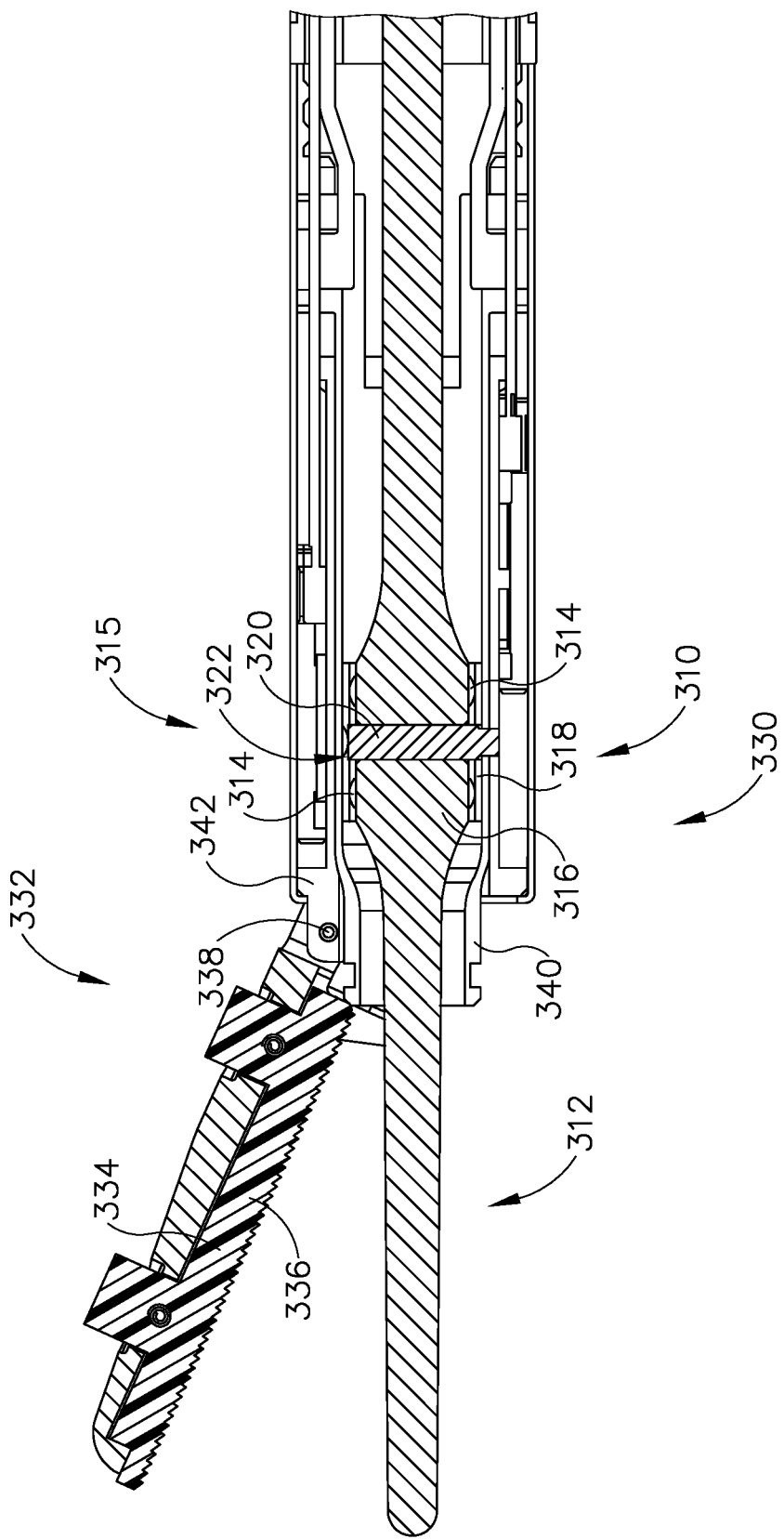
FIG. 32 depicts a cross-sectional view of a sixth ultrasonic surgical instrument with the acoustic waveguide and ultrasonic blade of FIG. 30 incorporated therein.

FIG. 32 shows acoustic waveguide (310) and ultrasonic blade (312) incorporated into an exemplary sixth ultrasonic surgical instrument (330). As mentioned above, an exterior of compression sleeve (308) makes contact with a translating clamp arm drive (340) such that translating clamp arm drive (340) may longitudinally actuate relative to compression sleeve (318) and the rest of distal flange (315), while compression sleeve (318) still provides sufficient compression on overmold rings (314) between sleeve (318) and waveguide flange portion (316) to provide for the above mentioned benefits. Therefore, translating clamp arm drive (340) may translate in order to pivot clamp arm (334) and clamp pad (336) about pivot pin (338) relative to distal tongue (342) between an open and closed position in accordance with the description herein, while containing distal flange (315) to provide for the benefits described above. Translating clamp arm drive (340) may define a slot in which distal waveguide pin (320) is disposed such that clamp arm drive (340) may translate without waveguide pin (320) obstructing such translation. Distal tongue (342) may also be configured to clock clamp arm (334) in accordance with the description above, such that distal tongue (342) rotates around translating clamp arm drive (340).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector, wherein the end effector comprises: (i) an ultrasonic blade, and (ii) a clamp arm configured to move relative to the ultrasonic blade between an open position and a closed position; (b) a shaft assembly, comprising: (i) a proximal shaft portion extending along a longitudinal axis, (ii) an acoustic waveguide extending proximally from the ultrasonic blade, wherein the acoustic waveguide comprises a flexible portion, (iii) a distal shaft portion extending along a distal axis, and (iv) an articulation section interposed between the proximal shaft portion and the distal shaft portion, wherein the flexible portion of the acoustic waveguide extends along the articulation section, wherein the articulation section is configured to deflect the distal shaft portion and the end effector relative to the longitudinal axis between a non-deflected position and a deflected position; and (c) an axial location feature configured to inhibit the ultrasonic blade from shifting relative to the clamp arm along the distal axis as the end effector is driven between the non-deflected position and the deflected position.

Example 2

The surgical instrument of Example 1, wherein the axial location feature comprises an axial locating slot defined by the ultrasonic blade and a protrusion associated with the clamp arm, wherein the protrusion is housed within the axial locating slot.

Example 3

The surgical instrument of Example 2, wherein the distal shaft portion comprises a distal tongue, wherein the clamp arm is pivotably coupled with the distal tongue via a pivot pin.

Example 4

The surgical instrument of Example 3, wherein the distal tongue defines a longitudinal slot, wherein the pivot pin is housed within the longitudinal slot.

Example 5

The surgical instrument of Example 4, wherein the pivot pin is configured to translate within the slot in response to the axial location feature inhibiting the ultrasonic blade form shifting relative to the clamp arm.

Example 6

The surgical instrument of any one or more of Examples 3 through 5, wherein the distal shaft portion comprises an outer shaft, wherein the distal tongue is attached to the outer shaft.

Example 7

The surgical instrument of any one or more of Examples 1 through 6, wherein the shaft assembly further comprises a clamp arm closure drive configured to move the clamp arm between the open position and the closed position.

Example 8

The surgical instrument of Example 7, wherein the clamp arm closure drive comprises a slot, wherein a protrusion of the clamp arm is housed within the slot.

Example 9

The surgical instrument of any one or more of Examples 1 through 8, wherein a proximal portion of the waveguide comprises a pin, wherein the proximal shaft portion comprises a shaft defining an elongated slot, wherein the pin is housed within the elongated slot.

Example 10

The surgical instrument of any one or more of Examples 1 through 10, wherein the axial location feature comprises a distal tongue coupled with a distal flange of the waveguide.

Example 11

The surgical instrument of Example 10, wherein the distal tongue is coupled with the distal flange via a waveguide pin.

Example 12

The surgical instrument of Example 11, wherein the distal tongue defines a circumferential slot, wherein the waveguide pin is ratably housed within the circumferential slot.

Example 13

The surgical instrument of Example 12, wherein the distal tongue is pivotably coupled with the clamp arm.

Example 14

The surgical instrument of Example 13, wherein the distal tongue is configured to clock the clamp arm around the ultrasonic blade between a first clocked position and a second clocked position.

Example 15

The surgical instrument of Example 14, wherein the distal shaft portion comprises an outer shaft, wherein the distal tongue is slidably disposed within the outer shaft.

Example 16

A surgical instrument, comprising: (a) an end effector, wherein the end effector comprises: (i) an ultrasonic blade, and (ii) a clamp arm configured to move relative to the ultrasonic blade between an open position and a closed position; (b) a shaft assembly, comprising: (i) a proximal shaft portion extending along a longitudinal axis, (ii) an acoustic waveguide extending proximally from the ultrasonic blade, wherein the acoustic waveguide comprises a flexible portion, (iii) a distal shaft portion extending along a distal axis, and (iv) an articulation section interposed between the proximal shaft portion and the distal shaft portion, wherein the articulation section is configured to bend the flexible portion of the acoustic waveguide along a first arc length and deflect the distal shaft portion along a second arc length in order to drive the end effector into a deflected position; and (c) an axial location feature configured to inhibit the ultrasonic blade from shifting relative to the clamp arm along the distal axis as the end effector is driven into the deflected position.

Example 17

The surgical instrument of Example 16, wherein the axial locating feature couples the ultrasonic blade with the clamp arm.

Example 18

The surgical instrument of any one or more of Examples 16 through 17, wherein the axial locating feature couples a translating distal tongue with a distal flange of the acoustic waveguide.

Example 19

A surgical instrument, comprising: (a) an end effector, wherein the end effector comprises: (i) an ultrasonic blade, and (ii) a clamp arm configured to move relative to the ultrasonic blade between an open position and a closed position; (b) a shaft assembly, comprising: (i) a distal shaft portion extending along a distal axis, and (ii) an articulation section, wherein the articulation section is configured to bend the ultrasonic blade along a first arc length and deflect the distal shaft portion along a second arc length in order to drive the end effector into a deflected position; and (c) an axial location feature configured to inhibit the ultrasonic blade from shifting relative to the clamp arm along the distal axis as the end effector is driven into the deflected position.

Example 20

The surgical instrument of Example 19, wherein the articulation section comprise a pair of translating bands configured to translate in opposing directions.

IV. Miscellaneous

Any one or more of the teaching, expressions, embodiments, examples, etc. described herein may be combined with any one or more of the teachings, expressions, embodiments, examples, etc. described in U.S. patent application Ser. No. 16/556,661, entitled "Ultrasonic Surgical Instrument with a Multi-Planar Articulating Shaft Assembly," filed on Aug. 30, 2019, published as U.S. Pub. No. 2021/0059709 on Mar. 4, 2021; U.S. patent application Ser. No. 16/556,667, entitled "Ultrasonic Transducer Alignment of an Articulating Ultrasonic Surgical Instrument," filed on Aug. 30, 2019, published as U.S. Pub. No. 2021/0059710 Mar. 4, 2021; U.S. patent application Ser. No. 16/556,625, entitled "Ultrasonic Surgical Instrument with Axisymmetric Clamping," filed on Aug. 30, 2019, published as U.S. Pub. No. 2021/0059707 on Mar. 4, 2021; and/or U.S. patent application Ser. No. 16/556,727, entitled "Rotatable Linear Actuation Mechanism," filed on Aug. 30, 2019,published as U.S. Pub. No. 2021/00599711 on Mar. 4, 2021. The disclosure of each of these applications is incorporated by reference herein.

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874; U.S. Pub. No. 2007/0191713; U.S. Pub. No. 2007/0282333; U.S. Pub. No. 2008/0200940; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265; U.S. Pat. No. 9,393,037, issued Jul. 19, 2016; U.S. Pat. No. 10,172,636, issued Jan. 8, 2019; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into another example of a robotic surgical system, and those of ordinary skill in the art will recognize that various teachings herein may be readily combined with various teachings of any of the following. U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector, wherein the end effector comprises:
      (i) an ultrasonic blade, and
      (ii) a clamp arm configured to move relative to the ultrasonic blade between an open position and a closed position;
   (b) a shaft assembly, comprising:
      (i) a proximal shaft portion extending along a longitudinal axis,
      (ii) an acoustic waveguide extending proximally from the ultrasonic blade, wherein the acoustic waveguide comprises a flexible portion,
      (iii) a distal shaft portion extending along a distal axis, and
      (iv) an articulation section interposed between the proximal shaft portion and the distal shaft portion, wherein the flexible portion of the acoustic waveguide extends along the articulation section, wherein the articulation section is configured to deflect the distal shaft portion and the end effector relative to the longitudinal axis between a non-deflected position and a deflected position; and
   (c) an axial location feature configured to inhibit the ultrasonic blade from shifting relative to the clamp arm along the distal axis as the end effector is driven between the non-deflected position and the deflected position, wherein the axial location feature comprise a distal tongue coupled with a distal flange of the waveguide, wherein the distal tongue is coupled with the distal flange via a waveguide pin, wherein the distal tongue defines a circumferential slot, wherein the waveguide pin is rotatably housed within the circumferential slot.

2. The surgical instrument of claim 1, wherein the shaft assembly further comprises a clamp arm closure drive configured to move the clamp arm between the open position and the closed position.

3. The surgical instrument of claim 2, wherein the clamp arm closure drive comprises a slot, wherein a protrusion of the clamp arm is housed within the slot.

4. The surgical instrument of claim 1, wherein a proximal portion of the waveguide comprises a pin, wherein the proximal shaft portion comprises a shaft defining an elongated slot, wherein the pin is housed within the elongated slot.

5. The surgical instrument of claim 1, wherein the distal tongue is pivotably coupled with the clamp arm.

6. The surgical instrument of claim 5, wherein the distal tongue is configured to clock the clamp arm around the ultrasonic blade between a first clocked position and a second clocked position.

7. The surgical instrument of claim 6, wherein the distal shaft portion comprises an outer shaft, wherein the distal tongue is slidably disposed within the outer shaft.

8. A surgical instrument, comprising:
   (a) an end effector, wherein the end effector comprises:
      (i) an ultrasonic blade, and
      (ii) a clamp arm configured to move relative to the ultrasonic blade between an open position and a closed position;
   (b) a shaft assembly, comprising:
      (i) a proximal shaft portion extending along a longitudinal axis, (ii) an acoustic waveguide extending proximally from the ultrasonic blade, wherein the acoustic waveguide comprises a flexible portion, (iii) a distal shaft portion extending along a distal axis, and (iv) an articulation section interposed between the proximal shaft portion and the distal shaft portion, wherein the articulation section is configured to bend the flexible portion of the acoustic waveguide along a first arc length and deflect the distal shaft portion along a second arc length in order to drive the end effector into a deflected position; and (c) an axial location feature configured to inhibit the ultrasonic blade from shifting relative to the clamp arm along the distal axis as the end effector is driven into the deflected position, wherein the axial location feature comprises a distal tongue fixed to a distal flange of the acoustic waveguide, wherein the distal tongue is pivotally attached to the clamp arm via a pin such that the clamp arm is configured to pivot relative to the distal tongue about the pin.

9. The surgical instrument of claim 8, wherein the axial locating feature couples the ultrasonic blade with the clamp arm.

10. The surgical instrument of claim 8, wherein the axial locating feature couples a translating distal tongue with a distal flange of the acoustic waveguide.

11. A surgical instrument, comprising:
(a) an end effector, wherein the end effector comprises:
 (i) an ultrasonic blade, and
 (ii) a clamp arm configured to move relative to the ultrasonic blade between an open position and a closed position;
(b) a shaft assembly, comprising:
 (i) a distal shaft portion extending along a distal axis, and
 (ii) an articulation section, wherein the articulation section is configured to bend the ultrasonic blade along a first arc length and deflect the distal shaft portion along a second arc length in order to drive the end effector into a deflected position; and
(c) an axial location feature configured to inhibit the ultrasonic blade from shifting relative to the clamp arm along the distal axis as the end effector is driven into the deflected position, wherein the axial location feature comprises a distal tongue fixed to the ultrasonic blade and pivotally coupled to the clamp arm, wherein the distal tongue is configured to clock the clamp arm around the ultrasonic blade between a first clocked position and a second clocked position.

12. The surgical instrument of claim 11, wherein the articulation section comprise a pair of translating bands configured to translate in opposing directions.

* * * * *